(12) United States Patent
Barney

(10) Patent No.: US 7,331,340 B2
(45) Date of Patent: Feb. 19, 2008

(54) MEDICAMENT DISPENSING DEVICE WITH A DISPLAY INDICATIVE OF THE STATE OF AN INTERNAL MEDICAMENT RESERVOIR

(75) Inventor: Brian Barney, Great Dunmow (GB)

(73) Assignee: Ivax Corporation, Miami, FL (US)

( * ) Notice: Subject to any disclaimer, the term of this patent is extended or adjusted under 35 U.S.C. 154(b) by 9 days.

(21) Appl. No.: 10/793,150

(22) Filed: Mar. 4, 2004

(65) Prior Publication Data

US 2005/0081846 A1    Apr. 21, 2005

Related U.S. Application Data

(60) Provisional application No. 60/452,260, filed on Mar. 5, 2003.

(30) Foreign Application Priority Data

Mar. 4, 2003  (GB) ................................. 0304905.3
Jan. 26, 2004 (GB) ................................. 0401649.9

(51) Int. Cl.
*A61M 11/00* (2006.01)

(52) U.S. Cl. ........................... 128/200.23; 128/203.15; 128/205.23; 128/203.12; 128/200.19; 128/200.21

(58) Field of Classification Search ........... 128/200.11, 128/200.12, 200.14, 200.16, 200.19, 200.21–200.24, 128/202.22, 203.12–203.15, 203.21, 203.23, 128/204.18, 205.23, 207.14; 116/200, 202, 116/279, 306; 239/338
See application file for complete search history.

(56) References Cited

U.S. PATENT DOCUMENTS

| | | | |
|---|---|---|---|
| 5,404,871 A * | 4/1995 | Goodman et al. | 128/200.14 |
| 5,447,150 A | 9/1995 | Bacon | |
| 5,544,647 A | 8/1996 | Jewett et al. | |
| 5,622,163 A | 4/1997 | Jewett et al. | |
| 6,138,669 A * | 10/2000 | Rocci et al. | 128/200.23 |
| 6,431,168 B1 | 8/2002 | Rand et al. | |
| 6,446,627 B1 | 9/2002 | Bowman et al. | |
| 2002/0189612 A1 * | 12/2002 | Rand | 128/200.23 |

* cited by examiner

*Primary Examiner*—Patricia Bianco
*Assistant Examiner*—Nihir Patel
(74) *Attorney, Agent, or Firm*—Lerner, David, Littenberg, Krumholz & Mentlik, LLP

(57) ABSTRACT

A metered dose inhaler for use with a removable pressurized aerosol canister, or reservoir, having a display for indicating to a user the state of the canister. A memory device on the canister or a housing which houses the canister stores information indicative of doses dispensed from, or remaining in, the canister. That information is processed to provide and display information representative of the state of the canister.

32 Claims, 18 Drawing Sheets

MEDICAMENT DISPENSING DEVICE WITH A DISPLAY INDICATIVE OF THE STATE OF AN INTERNAL MEDICAMENT RESERVOIR

CROSS-REFERENCE TO RELATED APPLICATIONS

The present application claims priority to provisional U.S. patent application Ser. No. 60/452,260, filed Mar. 5, 2003, and United Kingdom Patent Application Serial Number 0304905.3, filed Mar. 4, 2003, and United Kingdom Patent Application Serial Number 0401649.9, filed Jan. 26, 2004.

FIELD OF THE DISCLOSURE

This disclosure relates to a medicament dispensing device, and more specifically, to a device suitable for dispensing discrete or metered amounts, or metered doses, of fluid medicament from a reservoir, and having a display for indicating to the user, the state of the medicament reservoir.

BACKGROUND OF THE DISCLOSURE

Metered dose inhalers are well known in medicine for treatment, or alleviation of the effects of respiratory complaints, such as asthma. Breath-actuated devices are also known, and have been the subject of many patents.

Many inhalation-actuated dispensing devices are made for use with a pressurized aerosol dispensing container. The dispensing container includes a valve that is normally capable of releasing a metered amount of the aerosol contents, when an internal spring operating the valve is compressed by a sufficient amount. The dispensing device often comprises a chamber having a mouthpiece, air inlets, actuating means for causing the actuation of the valve in the dispensing container, a latching means for releasably retaining said metering valve in a charged position, and an inhalation responsive means for releasing the latch, such that a metered amount of aerosol compound is discharged into the region of the mouthpiece. The overall objective is to give co-ordination of discharge of medicament from the aerosol container with inhalation of the patient, thus allowing a maximum dose of medicament to reach the bronchial passages of the lungs.

U.S. Pat. No. 5,447,150, which is assigned to the assignee of the present disclosure and incorporated by reference herein, discloses a metered dose inhaler. Release of the medicament is actuated through inhalation by a patient through an inhalation-actuated device of the inhaler of the '150 patent.

Prior art inhalers typically include a housing, into which the aerosol medicament canister is removably placed. The canister includes a nozzle at one end which is supported by a structure providing an air flow path leading to a patient-accessible mouthpiece. In many of the prior art inhalers, the aerosol canister is removable from the inhaler housing to permit effective cleaning of the structure defining the airflow path. In some inhalers, the housing is designed to accept a succession of user-introduced aerosol medicament canisters, as well as to provide for canister removal for cleaning.

In the use of these devices, it is desirable that the user know whether the canister in, or about to be placed in, the user's inhaler has an ample supply of doses of medicament for the near term, as well as for the longer term. With that information, a user would know when to replace a given medicament canister.

In the prior art, there have been efforts to obtain and, make available to a user, information indicative of the number of doses dispensed from, or remaining in, a medicament inhaler. By way of example, U.S. Pat. No. 6,446,627, which is also assigned to the assignee of the present disclosure, shows a mechanical counter assembly that is disposed on the housing of an inhaler, where the counter assembly indicates (by way of a visible-to-a-user counter display) a number corresponding to the number of doses dispensed from, or remaining, in a medicament canister. Upon as actuation pursuant to which a dose is dispensed, the counter is driven to increment (in the case where number of doses dispensed doses is indicated, or to decrement in the case where the number of doses remaining is indicated) by way of a mechanical linkage driven by a moving part in the inhaler (for example, motion of the canister relative to the nozzle, in the case of a breath-actuated inhaler of the type described in conjunction with FIGS. 3-6 of U.S. Pat. No. 5,447,150).

While such mechanical count/actuation assemblies do indicate dose count actuation information to a user, subsequently developed prior art inhalers indicate similar information through electronic and/or electromechanical dose counter and indicator assemblies. By way of example, U.S. Pat. Nos. 5,622,163 and 5,544,647 disclose closed capsules, one mounted on a sleeve of an inhaler housing and the other mounted on a base of an aerosol medicament canister. In those patents, the entire dose counter/indicator assembly is a unitary structure, disposed in a closed capsule. Moreover, those disclosed assemblies include a liquid crystal display (LCD) which indicates a multidigit number representative of doses dispensed or remaining in the canister.

Another prior art inhaler with an electronic and/or electromechanical dose counter and indicator assembly is disclosed in U.S. Pat. No. 6,431,168. That patent discloses unitary electronic and/or electromechanical dose counter/actuation indicator assemblies, within a closed or sealed capsule, and having a multidigit LCD for indicating to a user the number of doses dispensed from, or remaining in, an aerosol medicament canister. The electromechanical dose counter indicator assembly is affixed to the canister at the nozzle end of the canister.

In all cases of the above referenced patents, the indication provided to the user by the display, is in the form of a number (of doses dispensed, or doses remaining). In those disclosures, the counter and indicated number is incremented, or decremented, in response to delivery of a dose, or an "actuation" of the inhaler, Thus, to the extent the display indicates "actuation" to the user, such indication must be determined by the user's observation of a transition of the displayed count from one number to the next. Further, there is no information displayed to the user which is directly indicative of the "state of canister", that is, whether it is "safe" to use (with an adequate number of remaining doses) in a "warning" zone (with a small number of doses left), or in a "danger" zone (with no doses left). The user must draw his/her own conclusions as to the "state of the canister", by observing the number (not always an easily performed task, particularly by a user with compromised vision or mental abilities) and then determining whether the observed count is in the "safe", "warning" or "danger" zone.

Moreover, in some of these prior art patents a unitary electronic and/or electromechanical dose counter and actuation indicator assembly is affixed directly to the canister, which in the case of inhaler systems for which it is intended that multiple canisters be sequentially used in a single housing, is relatively costly, because each canister must have its own complete electronic and/or electromechanical dose counter and actuation indicator assembly.

It is an object of the present disclosure to provide a new and improved medicament inhaler having a device which provide an indication to a user of the state of a medicament canister contained in the inhaler.

It is a further object of the present disclosure to provide improved inhalers having canister-associated information stored on a canister for use in generating canister state information for display to a user.

Another object of the present disclosure is to provide improved inhalers with removable medicament reservoirs or canisters, permitting cleaning while providing, on user interrogation, information indicative of the state of the canister.

It is another object to provide inhalers which display to a user, information indicative of the general state of a replaceable medicament reservoir, or canister, contained within the inhaler.

Another object is to provide a medicament reservoir, or canister, bearing a user accessible interrogation assembly to provide information indicative of the state of the canister.

SUMMARY OF THE DISCLOSURE

The present disclosure provides an inhaler having a "state of the canister" indicator for a user. The inhaler may include an aerosol medicament inhaler device of the type disclosed in FIGS. 3-5 of U.S. Pat. No. 5,447,150, for example, or alternatively, other inhaler devices including a medicament-containing reservoir (referred to broadly herein as a "canister").

In one exemplary embodiment, the present disclosure provides a medicament inhaler assembly including a housing defining a central void region disposed along a central axis, and a medicament container having an internal medicament containing reservoir, and extending along a container axis, and having at one end thereof, a dispensing port extending along the container axis and coupled to the reservoir. The inhaler also includes means for supporting the medicament container within the central void region of the housing with the container axis substantially coaxial with the central axis of the housing, whereby a user-induced motion in a predetermined amount of the container relative to the housing in a first direction along the central axis causes medicament to be dispensed from the dispensing port.

The inhaler also includes identification means attached to the container for presenting information indicative of an identity of the container, the identity being associated with the housing, and a detector attached to the housing and adapted to detect the presented information when the container is disposed in the central void region of the housing. The detector also generates a VALID signal when the detected presented information of the container corresponds to the identity information associated with the housing, and an INVALID signal otherwise. A container state indicator is attached to the housing and includes means responsive to the VALID signal for detecting the medicament dispensing motions of the container relative to the housing, and for generating a user-readable signal indicative of the state of the container.

In another exemplary form, the inhaler of the disclosure displays, i.e., indicates, color-coded information to a user. For example, an illuminated green light emitting diode (LED) is indicative of a canister being in a "safe" zone, where the user does not have to be concerned about the adequacy of the number of doses remaining in the canister, an illuminated yellow LED is indicative of a "caution" to the user that there is a relatively small number of doses remaining in the canister and that replacement of the canister should be considered, and an illuminated red LED is indicative of the canister being depleted. In that exemplary form, the green, yellow and red LED's might be replaced with multiple single color LED's with suitable green, yellow and red filters. The device may also use an LCD, instead of the LED.

With this exemplary configuration, the user is provided with an indication, not of the number of doses dispensed or remaining, but rather of the information the user really needs, namely, the state of the canister, "safe", "caution" or "warning" (i.e., no doses remaining). In the prior art, the user had to actively deduce this information, often a difficult task for a user with compromised vision, or impaired thought processes. With the present disclosure, the user only has to recognize a green, yellow or red light (and does not have to discern a multidigit number and logically determine whether it is indicative the canister being in a "safe", "caution" or "warning" state).

The display is controlled by a counter, which is preferably mounted on the housing of the inhaler for counting the number of doses that have been taken by the patient. The counter is responsive to the change of the state of a switch, which is responsive to relative motion between the canister and the housing.

In another exemplary form of the disclosure, the canister state indicator assembly is split into functional blocks, wherein a portion of that assembly is affixed to the canister (and moves with respect to the housing during dispensing of a dose) and a portion is affixed to the housing.

In one exemplary form of the disclosure, the canister state information is indicated to the user for only a relatively short time after a dose is dispensed in order to conserve battery energy. Alternatively, the canister state information is indicated to the user for only a relatively short time after the user performs a certain action (other than effecting a dose delivery) in order to conserve battery energy. Such actions may include "opening" of a hinged mouth piece cover of the inhaler, or depressing a housing-mounted "interrogation" switch.

In yet other forms of the disclosure, the canister may bear identification indicia, such as a bar code, or other machine readable indicia, which may be used by the canister state indicator to monitor dose delivery and display it to the user, and maintain electronic storage of that information on the canister.

In an alternative form, the dose delivery information is stored in a memory chip, which is mounted on the housing, and the counter is provided with a microprocessor programmed to recognize the identification indicia of the canister. Only when the microprocessor recognizes the identification indicia of the canister can the canister be used with the housing. Otherwise, the counter will show "error" or "empty" information on the display.

Additional aspects and advantages of the present disclosure will become readily apparent to those skilled in this art from the following detailed description, wherein exemplary embodiments of the present disclosure are shown and described, simply by way of illustration. As will be realized, the present disclosure is capable of other and different embodiments and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

For a fuller understanding of the nature and the objects of the present disclosure, reference should be made to the following detailed description and the accompanying drawings in which like reference numerals refer to like elements and in which.

DETAILED DESCRIPTION OF EXEMPLARY EMBODIMENTS

Figure 1:
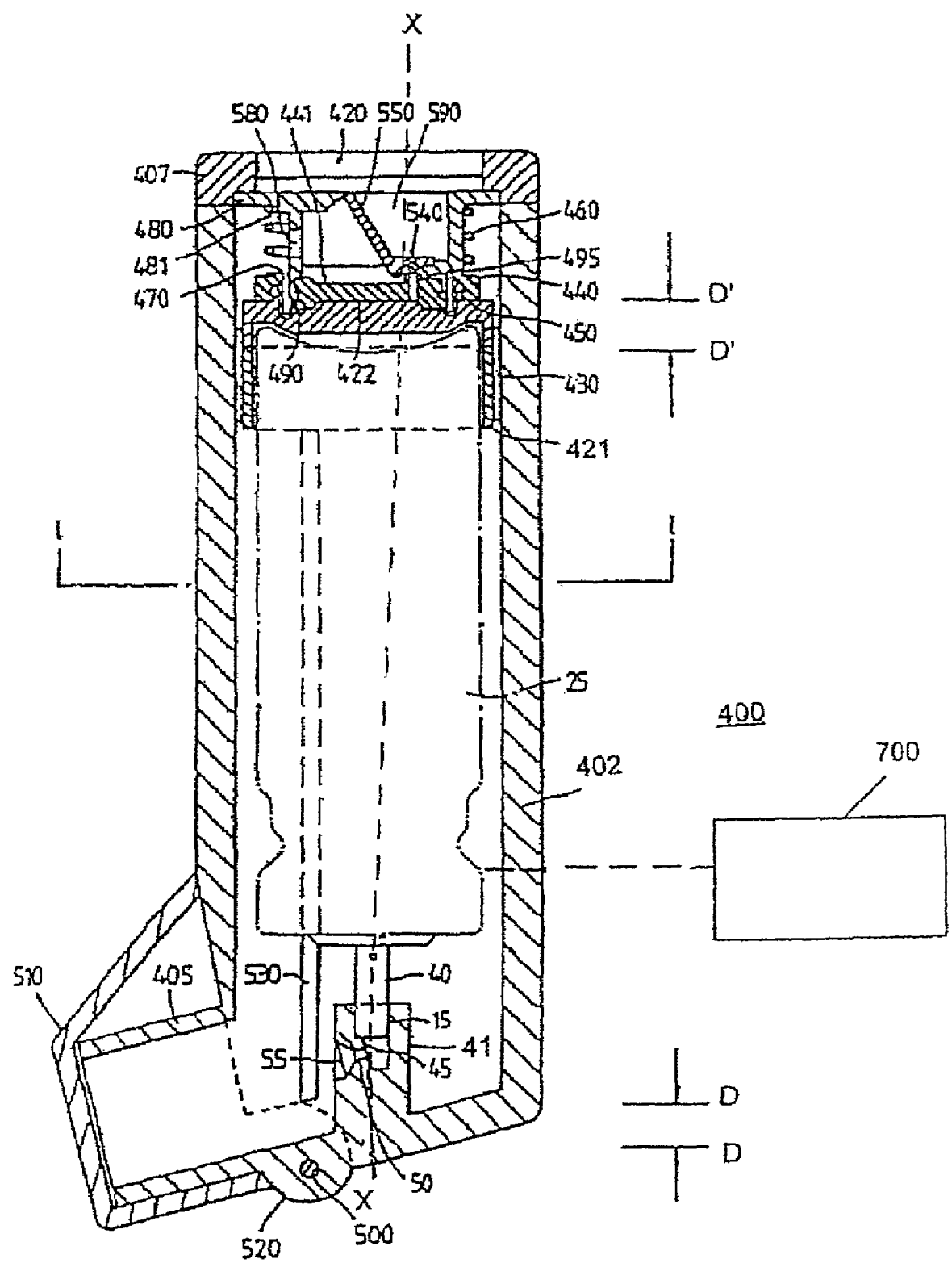
FIG. 1 is a partially section view, and partially in block diagram form, of an exemplary embodiment of medicament inhaler including an exemplary embodiment of a canister state indicating assembly according to the present disclosure.

An exemplary inhaler embodying the disclosure is shown in FIG. 1. That illustrated inhaler is a pneumatic force balance breath-activated inhaler of the general type shown in U.S. Pat. No. 5,447,150, but further includes a canister indicating assembly 700. Assembly 700 as indicated in general form in FIG. 1; detailed exemplary forms of assembly 700 are shown in FIGS. 5-8 described below.

In the arrangement shown in FIGS. 1-4, the inhalation device 400 consists of a main body, or housing, 402 which extending along an axis X-X and is generally cylindrical in cross section, with a mouthpiece section 405 at one end and an end cap 407 housing air inlets 420 at the other end. A known type of metered dose aerosol medicament dispensing container 25 of generally cylindrical shape extends along an axis Y-Y and is housed within the main body of the device. The aerosol medicament dispensing container has a stem 40 which contains an aerosol dispensing valve (not shown). The stem 40 is supported in a stemblock 41 extending from the housing 402. The bore 15 is such that it forms an air tight seal on the stem 40 of the aerosol dispensing container 25. A shoulder 45 limits and locates the position of the stem 40, which in turn locates the aerosol dispensing container 25 in position in the housing 402 such that the container 25 is substantially coaxial with the housing 402. A passage 50 extends from the bore 15, continuing from the shoulder 45 to interconnect with a dispensing nozzle 55.

The opposite end of the dispensing container 25 is contained within a sleeve 421 of similar cross section to the housing 402. The longitudinal axis of both the sleeve 421 and housing 402 is generally coaxial. The sleeve is in loose sliding contact with the inner wall of the main body and may include several rebated grooves 430 in its walls to allow free passage of air in the main body past the sleeve. The sleeve 421 may be held in place by connection with a diaphragm 440 held in connection with the top of the housing 402, as will now be described. Thus, the sleeve 421 effectively hangs from the top of the housing.

Figure 2A:
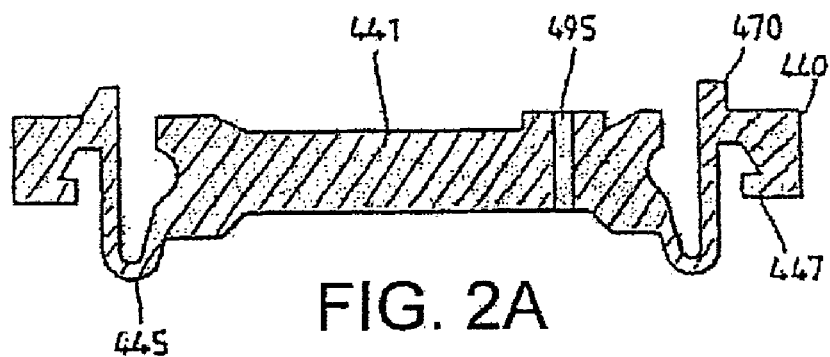
FIGS. 2A-2C show enlarged views of various embodiments of diaphragms for use with the inhaler FIG. 1.

One end of an exemplary molded flexible diaphragm 440 (as shown in FIG. 2A) comprising a rigid disc-like section 441, a flexible generally cylindrical wall section 445 and a stiffer connector section 447, is fitted around a purpose-made groove 450 in the sleeve, e.g., by snap-fitting. A further molded lip 470 on the diaphragm provides a snug fit for one end of a compression spring 460. The compression spring is thus located and free to act on the sleeve. The other end of the compression spring is located by an annular shoulder 481 in a predominantly cylindrical flanged insert 480 housed in the top section of the housing 402. This insert includes a groove 490 into which the disc-like section 441 of the flexible diaphragm 440 is snap-fitted.

Figure 2B:
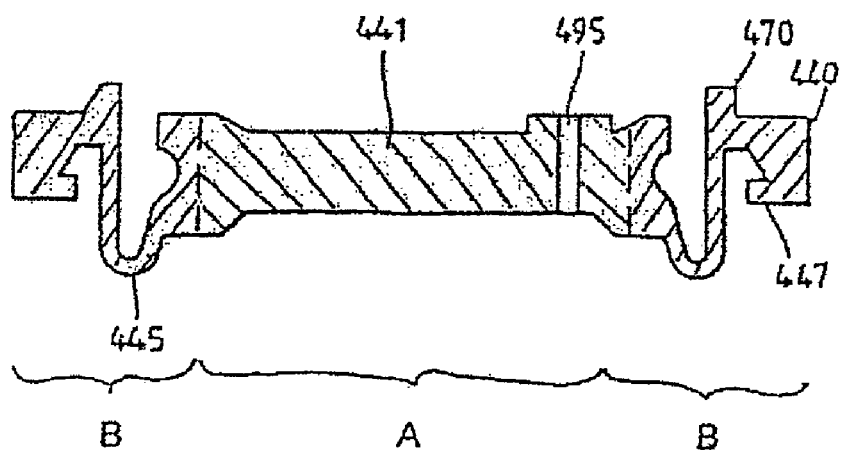
Figure 2C:
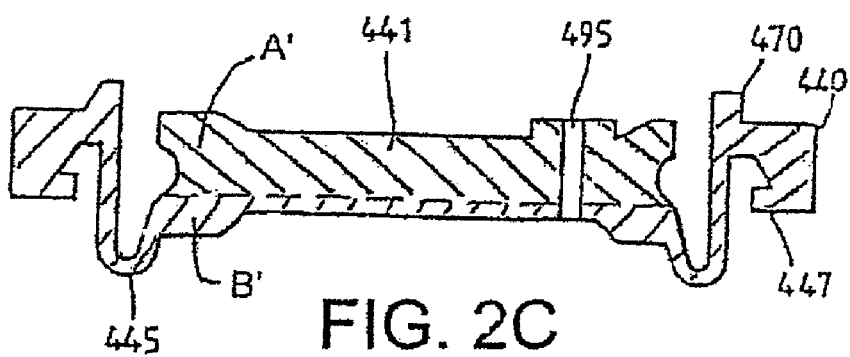
Figure 3:
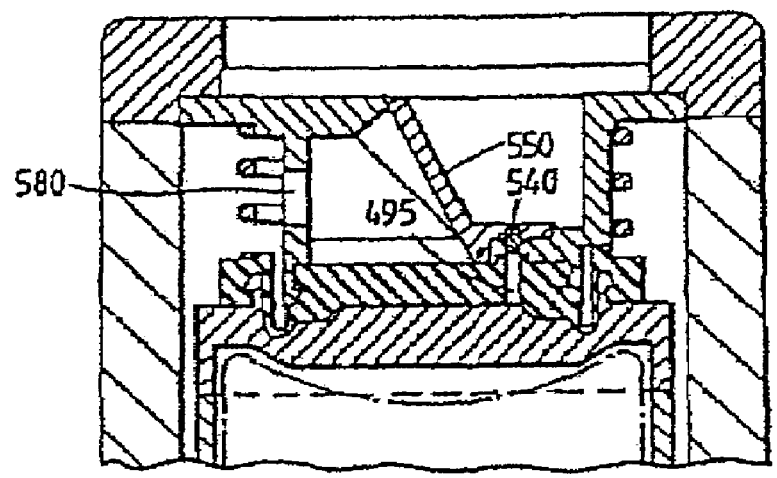
FIG. 3 shows an enlarged section view of the diaphragm in the inhaler of FIG. 1, shown positioned in a pre-actuated state.

Preferably, the diaphragm 440 is a multimaterial diaphragm (as shown in FIG. 2B and FIG. 2C, made by a multishot molding process wherein a first portion (such as the disk) is molded in a first step, and a second portion (such as the flexure and ring) is molded in a second step, and at the same time bonded to the first portion. The diaphragm may alternatively be molded in a single shot.

With the multimaterial diaphragm configuration shown in FIG. 2B, a relatively thick disk-portion "A" is molded from a rigid material (relatively high stiffness), which is particularly resistant to flexural deformation when the closed region 600 is at negative pressure, while the relatively thin flexure portion "B" is molded from an optimally flexible (relatively low stiffness) material, permitting high performance. The relatively thin flexure portion "B" is bonded to the disk-portion "A" along a continuous surface substantially parallel to the central axis of the diaphragm. FIG. 2C shows another embodiment of the multimaterial diaphragm, in which the disk-portion of the diaphragm 440 includes two layers A' and B', and one of the two layers A' and B' is made from a rigid material and the other one is made of a relatively flexible material.

The use of a rigid material for the disk portion of the diaphragm allows the section's thickness to be reduced without compromising stiffness of the disk portion, thus substantially reducing the molding cycle time required. One of skill in the art will appreciate that the use of equal sections in a component facilitates optimization and increases the efficiency of the molding process. In a exemplary form of the disclosure, the diaphragm is produced in a two-shot molding process with the disk being molded first, and then the flexure, so that the inner portion of the flexure is adjacent, and bonds to, the peripheral portion of the central disk. Alternative methods, such as compression molding of the flexure onto a rigid insert using vulcanizing materials, or casting of a silicone rubber onto a rigid insert may also be used.

The joint between the diaphragm connector section 447 and inner sleeve groove 450 is arranged to be air tight and the shape of the top surface of the sleeve 422 to conform to the internal shape of the diaphragm such that in the rest position of the inhaler the two surfaces are in close proximity, and the enclosed space between them very small.

The cylindrical insert 480 is retained in place by the end cap 407 fitted into the main body of the device. This forms a chamber 590 between the air inlet slots 420 and the rigid part 441 of the diaphragm. The chamber is provided with one or more air pathways 580 such that air may pass from the air inlet slots 420 to the mouthpiece 405. The rigid disc-like section 441 of the diaphragm also includes a small valve port 495 which is normally covered by a valve seal (flap) 540 housed in a vane 550 pivotally connected to the insert 480.

The vane 550 in its rest position divides the chamber 590 between the air inlets 420 and the air pathways 580 that link to the mouthpiece such that it may move from its rest position by means of a pressure drop between the air inlets and the mouthpiece. On movement of the vane to the actuated position the valve seal (flap) 540 is sufficiently moved to open the valve port 495. (The vane 550 may be biased closed by a light spring flexure, a weight or a magnet not shown.)

As shown in FIG. 1, the end of the housing 402 having a pivot 500 has a recess adapted to receive a cam 520 integral with a dust cap 510 operating on the pivot. The recess further includes a passage communicating with a similar passage molded into the internal wall of the housing 402. A camfollower 530 extending from the lower edge of the inner sleeve 421 acts on the cam such that when the dust cap is in the closed position the inner sleeve is forced by the camfollower to its uppermost position.

When the dust cap 510 is rotated to its open position, the cam profile is such that the camfollower is free to move downwards by an amount sufficient to allow actuation of the device.

In its rest position the dust cap 510 is closed, the camfollower 530 restrains the inner sleeve 421 in its uppermost position such that the enclosed space trapped between the diaphragm 440 and the top surface 422 of the inner sleeve is at a minimum and the spring 460 is compressed. The valve port 495 is closed by the valve seal (flap) 540 and the sleeve 421 is clear of the top of the aerosol can 25 which is thus unloaded.

The dust cap is opened rotating the integral cam 520 allowing the camfollower 530 to drop by amount DD. The inner sleeve is forced downwards under the action of the spring 460. As the inner sleeve moves downwards the enclosed volume between the diaphragm 440 and inner sleeve is increased by a linear equivalent amount D'D', less than or equal to DD. Since the valve port 495 is closed this creates a low pressure volume or near vacuum in the space 600 [FIG. 3]. The effect of the pressure differential between the enclosed volume 600 and atmospheric pressure is such that the inner sleeve tends to resist the action of the spring. As the inner sleeve moves downwards it contacts the aerosol can 25 and begins compression of the aerosol valve (not shown).

Downward movement of the inner sleeve will continue until there is a balance of forces between the compressive force in the spring 460 and resisting forces created by the pressure differential and compression of the aerosol valve. The geometry of the device is arranged such that this balance occurs before the aerosol valve has been sufficiently compressed to actuate it.

A typical aerosol requires from about 20 to 30 Newton's force to actuate. The spring 460 should accordingly provide a greater force, preferably 10% to 50% greater.

It may also be possible to arrange for the balance of forces to take place before the inner sleeve has contacted the aerosol can, such that the spring force is balanced by the resisting force produced oil the inner sleeve by virtue of the pressure differential.

Figure 4:
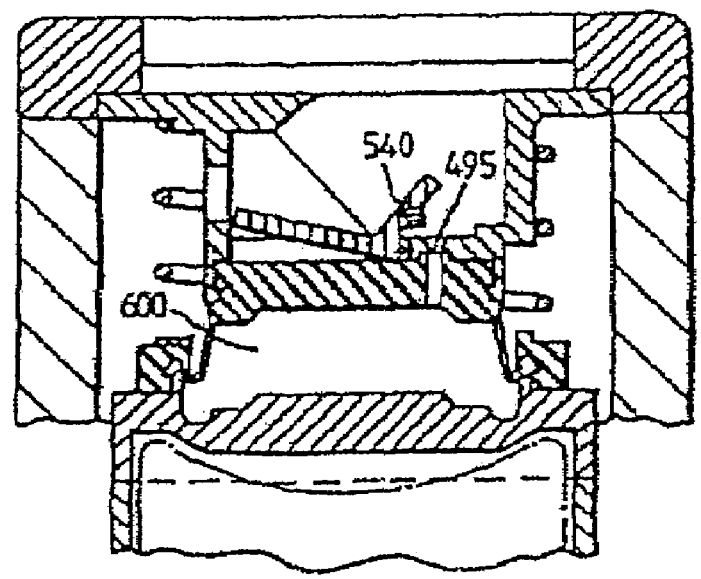
FIG. 4 shows an enlarged section view of the diaphragm in the inhaler of FIG. 1, shown positioned in an actuated state.

On inhalation by the patient through the mouthpiece 405, a small pressure differential is created across the vane 550 which is pivoted towards one end. The pressure differential causes the vane to move from the rest position to the actuated position as shown in FIG. 4. The vane and design of the air passageway 580 in the chamber 590 are such that in the actuated position air can flow freely from the air inlets 420 to the patient.

The movement of the vane 550 causes the valve seal (flap) 540 to be moved out of a sealing position with the valve port 495. Opening the valve port allows air into the gap 600 between the diaphragm and inner sleeve such that the enclosed space reaches atmospheric pressure. This causes an imbalance of forces acting on the sleeve 421 and container 25. The sleeve and container are thus forced downwards by the spring 460 resulting in the release of a measured dose of medicament through the dispensing nozzle 55 and into the mouthpiece at the same time as the patient breathes in. Thus the patient inhales air with a metered dose of medicament.

After the inhalation of the dose by the patient, the dust cap 510 is returned to its closed position. This rotates the cam 520 and causes the camfollower 530 to be forced upwards. This in turn acts on the inner sleeve 421 moving it upwards to compress the spring 460 and close the gap 600 between the diaphragm and inner sleeve top surface 422. This forces air out of the enclosed space 600 which escapes through the valve port 495 lifting the valve seal (flap) 540. Since the valve seal (flap) is only lightly biased to its closed position it presents little resistance to air flow out of the enclosed space. The aerosol can is free to return to the rest position under the action of its own aerosol valve spring.

Prior to use, a user loads the aerosol dispensing canister 25 into the housing 402. The aerosol canister 25 may be loaded by providing a coarse threaded screw in the housing 402, for example about the line I-I. When part of the housing 402 has been unscrewed, the aerosol canister 25 can be inserted. The housing 402 can then be replaced locating the inner sleeve over the top end of the canister 25 can, and the device 400 is ready for use. The device 400 could alternatively be manufactured as a sealed unit.

The device may be provided with means to provide a regulated air flow to the user or inhaler. Thus a sonic device, e.g., a reed, may be provided which sounds when the inspired air flow is greater than a pre-set level, e.g., above 30 to 50 litres per minute. The sonic device may be located in the mouthpiece 95 or below the air inlet 420. The sound produced warns the patient to breathe at a lower rate.

The device may also be provided with a means such that it will not operate below a certain pre-determined air flow rate, e.g., 10 to 30 liters per minute. In one embodiment the vane 550 will be biased by a spring such that the predetermined minimum air flow is necessary for it to move to its actuated position and enable the valve seal to open.

The main body of a dispensing device, as described in the above embodiment of this disclosure is preferably manufactured from a plastic such as polypropylene, acetal or molded polystyrene. It may however be manufactured from metal or another suitable material.

Figure 5:
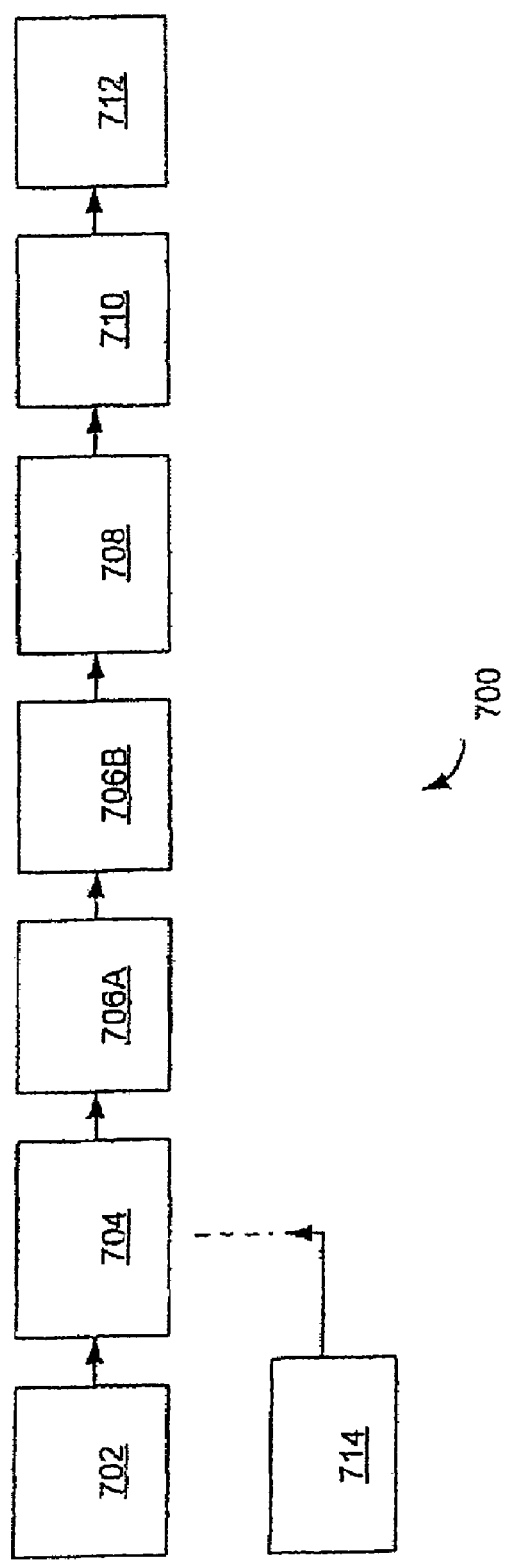
FIG. 5 shows in block diagram form, the exemplary canister state indicating assembly of the inhaler of FIG. 1.

In a exemplary form, the canister state indicator assembly 700 includes the elements shown in FIG. 5. The canister state indicator 700 is described below for use with an inhaler of the form shown in FIGS. 1-4 described below, but as will be apparent to those of skill in the art, can be readily adapted to other inhaler forms.

In FIG. 5, the exemplary canister state indicator 700 includes the following serially connected blocks: switch 702, counter 704, first memory 706A, second memory 706B, decoder 708, driver 710, display 712, and battery (power supply) 714. In the illustrated embodiment, elements 704, 706A, 706B, 708, 710 and 712 are all connected to and powered by battery 714. As illustrated in FIG. 5, battery 714 is a unitary element, but in various forms of the disclosure, battery 714 may comprise more than one battery, each powering one or more distinct ones of elements 704, 706A, 706B, 708, 710 and 712. Preferably, elements 704, 706A, 706B, 708, 710 and 712 are in the form of one or more application specific integrated circuits (ASICS) although those various circuit elements may have other conventional forms. Switch 702 is a device that is responsive to relative motion between the aerosol can (or canister) 25 and a nozzle in stem 40, for generating a short circuit between two electrodes, providing an "event" signal to counter 704.

In a exemplary form of the disclosure, the "event" is the dispensation of a dose. The switch 702 may be activated by direct axial motion of canister 25, or may be "side mounted" on the canister, so that as the canister moves axially, an element extending laterally from the interior of housing 402 causes activation of the switch 702.

The counter 704 is responsive to each event signal, as it occurs, to increment (or decrement) the counter, resulting in a count signal representative of the count state of the counter being stored in first memory 706A. As will be described below, the counter state signal is stored also in an optional (as described below) second memory 706B. The decoder 708 is responsive to the stored counter signal (in memory 706A or, optionally, 706B) to decode the count state signal to the form of decoder output signal representative of information to be displayed to a user. In a exemplary form, decoder 708 processes the counter state signal (as users were required to do in their minds with devices in the prior art) to determine whether the state of the counter is indicative of the canister being in a "safe", "caution", or "warning" state. In other forms of the disclosure, differing numbers of canister states, e.g., two or four, may be displayed. In the illustrated embodiment, the three states can be represented in a two bit binary signal. The decoder output signal is applied to drive 710 which converts the decoder output signal to the appropriate current and voltage levels to drive the display 714, which is responsive thereto, to illuminate a green, yellow, or red LED in accordance with the decoder output signal.

The switch/counter combination is operative in response to dose dispensations to increment (or decrement) in response to each dose, or actuation. However, in a exemplary form of the disclosure, the driver is adapted to only illuminate the display for a relatively short time (e.g., 10 seconds) after the occurrence of a different event, for example, closure of a switch (not shown) responsive to a mechanical motion (e.g., opening of cover 510), or depression of an "interrogate" switch (not shown).

The various elements of canister state indicator 700 may be on different locations in different embodiments of the disclosure . In cases where elements of assembly 700 are affixed to canister 25, those elements are supported in a can sleeve body 720, (preferably, but not necessarily) a one-piece structure, which is affixed to the canister 25. To accommodate electrical connections between element of assembly 700 on the canister 25 and on the housing 402, spring-loaded electrodes 722, 724 are preferably used to extend from the inner wall of housing 402, and contact electrodes 732, 734 on the other surface of body 720. Preferably, the contacts on body 720 extend fully about body 720 so that it is not necessary that the canister have any particular angular orientation.

Figure 6:
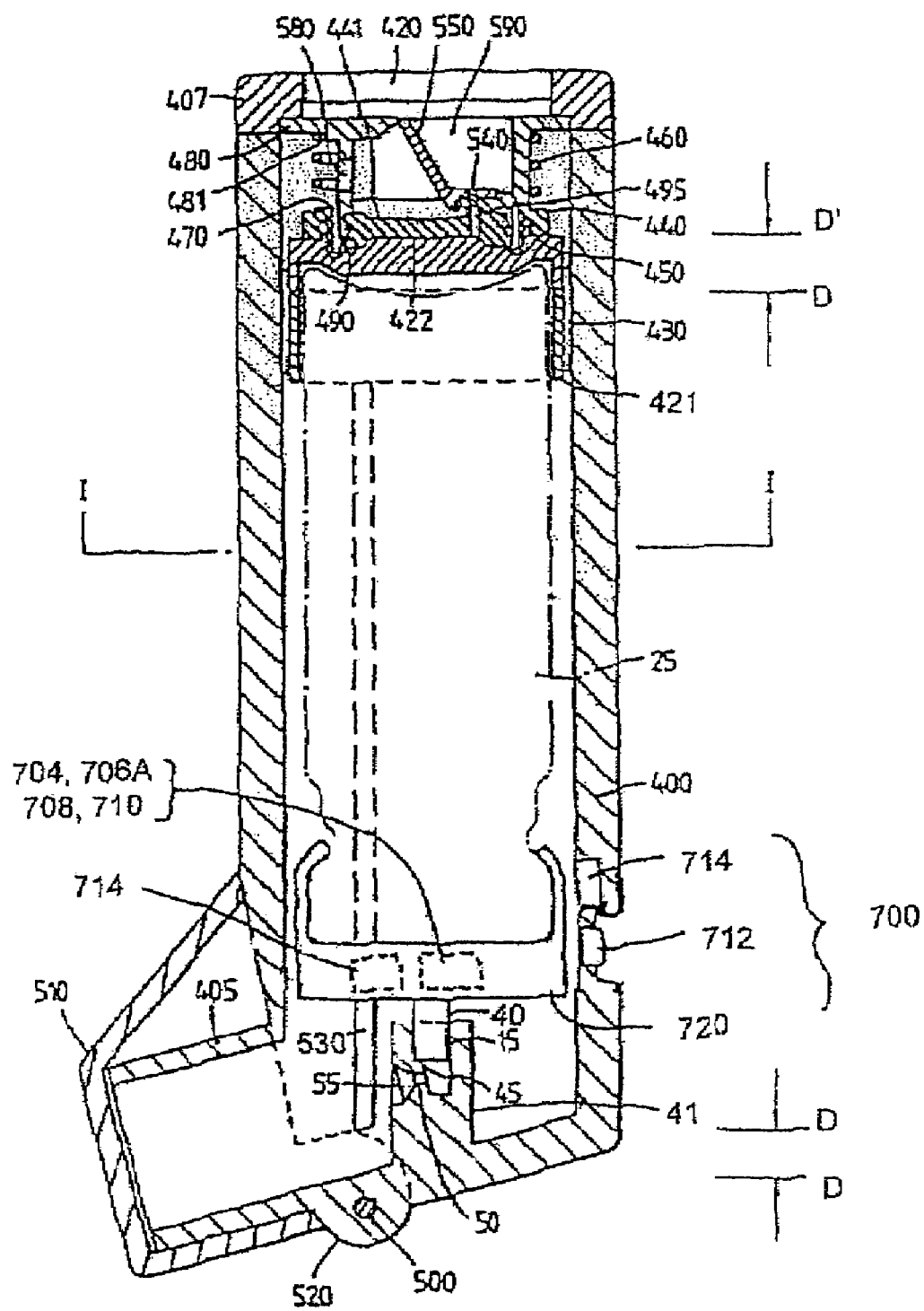
FIGS. 6-8 show sectional views of an exemplary embodiment of medicament inhaler including various exemplary embodiments of a canister state indicating assembly according to the present disclosure.
Figure 7:
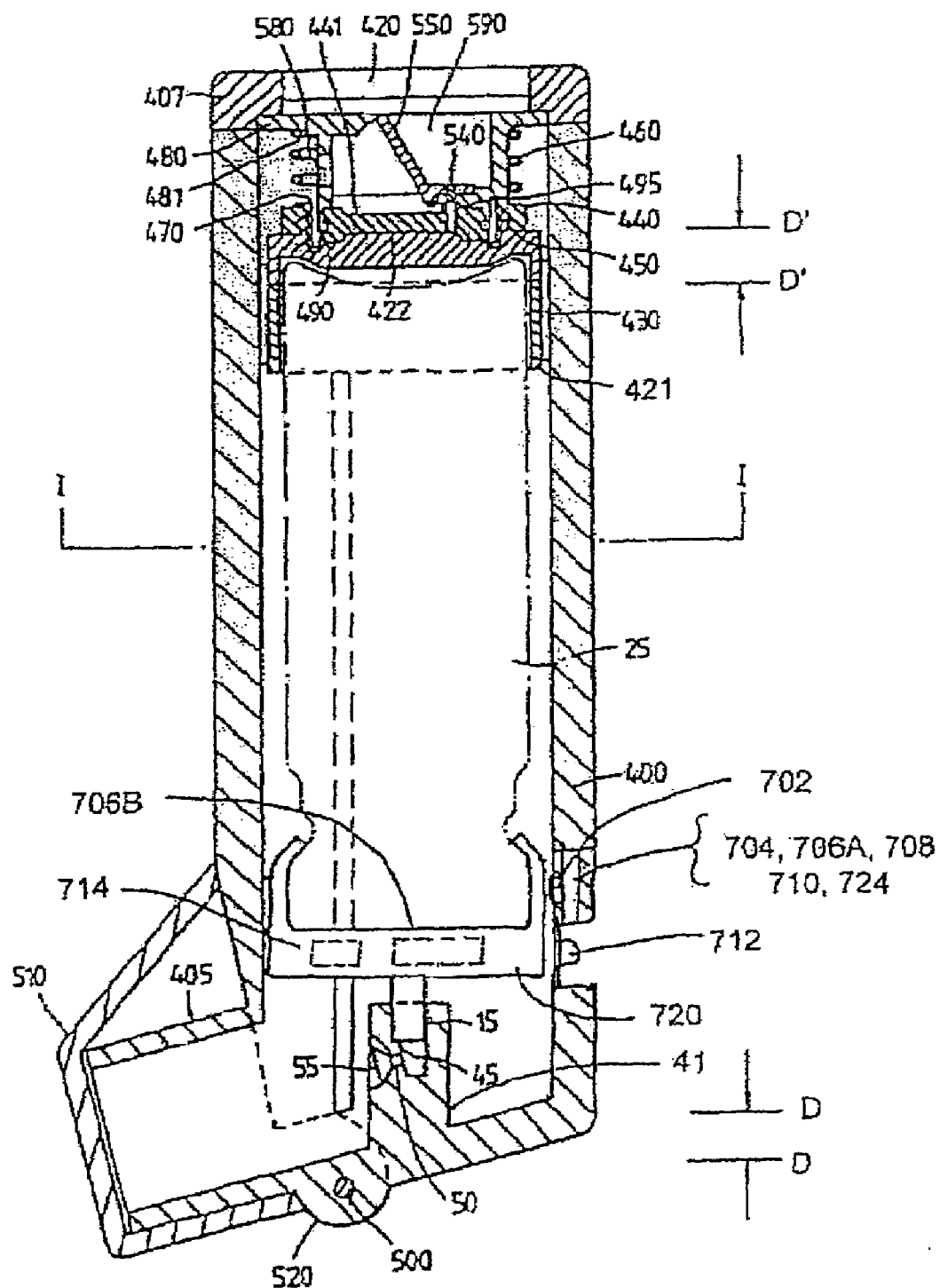
Figure 8:
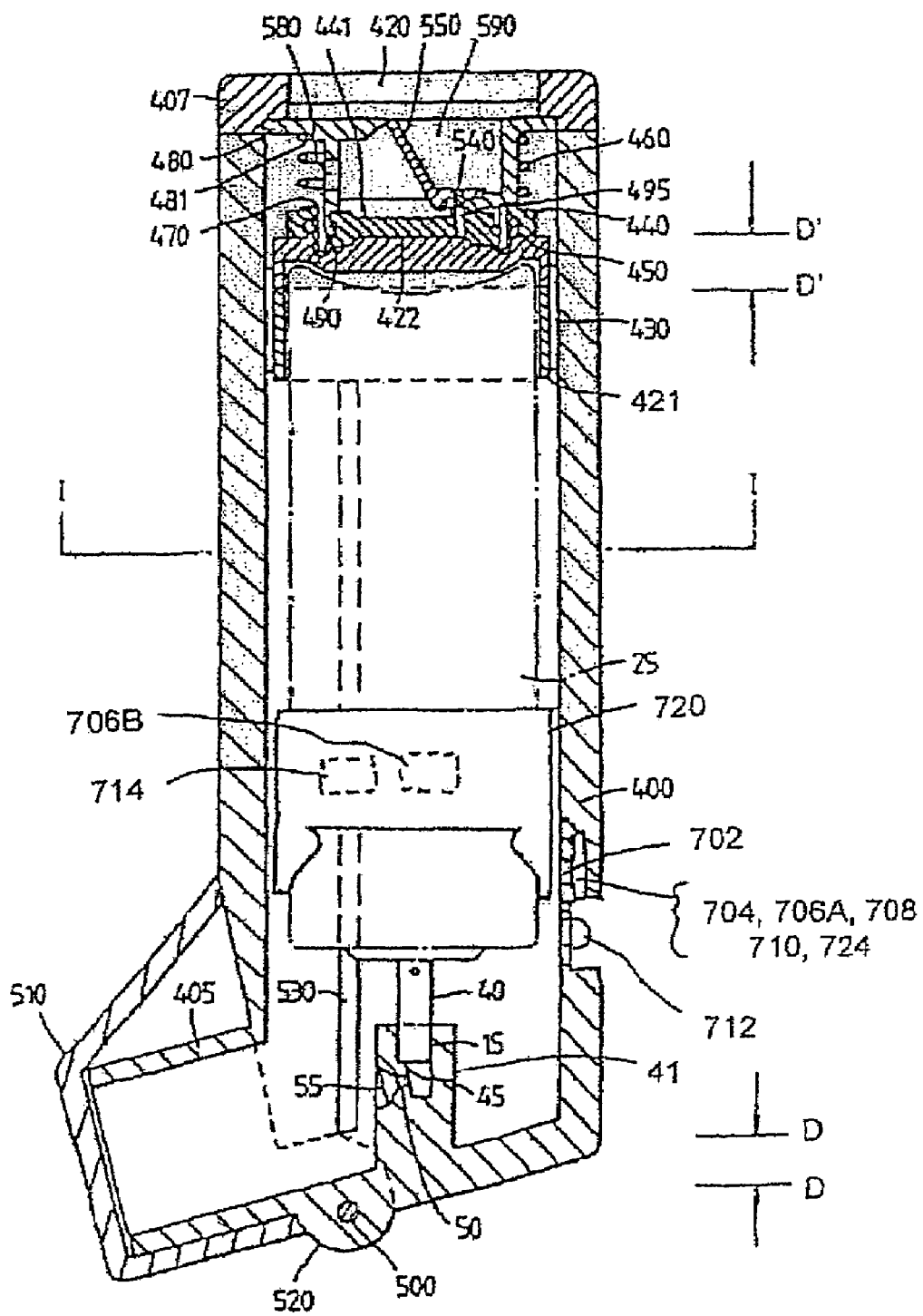

FIGS. 6-8 illustrate those such embodiments, but those are exemplary only; other configurations may be used in accordance with the disclosure.

In FIG. 6, display 712 is disposed on housing 402 and the remaining elements of assembly 700 are affixed to the canister 25, near the nozzle end of that canister. In this form, the optional second memory 706B is not used. With this configuration, the canister 25 includes, and keeps with it at all times, information representative of an accurate number of doses in (dispersed from) the canister 25. However, the indicator of the decoded count or signals, i.e., the LED's, are disposed on the housing. This reduces the cost of inhaler systems where multiple canisters are used, since only a single display (i.e., one set of LED's ) is used for multiple canisters.

FIG. 7 shows an alternative inhaler system which optimizes the component-saving advantage of the structure of the inhaler system of FIG. 6. In FIG. 7, the memory 706B and battery 714 are affixed (via body 720) to canister 25 and the remaining elements of assembly 700 are affixed to housing 402. In this configuration, with a canister in place within housing 402, the counter 704 is incremented (or decremented) as in the system of FIG. 6, and the state of the counter is stored in memory 706B on the canister 25. The battery 714 resides on the canister 25 and powers the memory 706B to maintain that signal, even if and when canister 25 is removed from housing 402. In this embodiment the counter 704 includes a processor 724 to detect replacement of the canister (after removal) into housing 402. Processor 724, upon sensing re-insertion of canister 25 into housing 402, loads counter 704 with the count signal stored in memory 706B.

Thereafter, actuations of the inhaler (i.e., dispensing of doses) causes counter 704 to increment (or decrement) its stored value, which is in turn transferred to memory 706B on canister 25, so that the value stored on the canister accurately represents the number of doses dispensed (or remaining in) canister 25. That number is decoded and processed into the color-coded "canister state" information, which is indicated to the user.

FIG. 8 shows another embodiment in which the body 720 is in the form of a cylindrical sleeve affixed to the canister 25, between the nozzle end and base of canister 25. In the illustrated form of FIG. 8, the disposition of components is the same as for the embodiment of FIG. 7, but other configurations, such as that shown in FIG. 6 may be used. The sleeve structure of body 720 provides a relatively large elongated structure, permitting easy assembly of electrical contacts between components on body 720 and components of housing 402.

In the configuration of FIGS. 7 and 8, only a single battery is used, which is canister-mounted. When the canister is positioned in housing 402, the battery is electrically coupled to provide power, in addition to memory 706B, to the other components of assembly 700. In other forms of the disclosure, battery 714 may include a first battery in body 720 and a second battery on housing 402.

Figure 9:
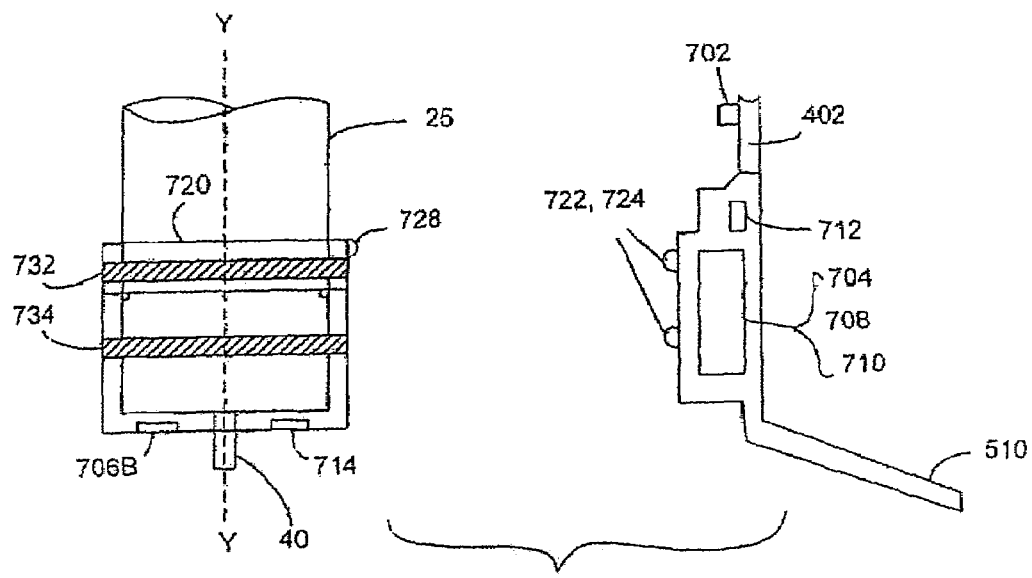
FIGS. 9 and 10 show sectional views of exemplary electrical connections for the embodiments of the canister state indicating assemblies of FIGS. 7 and 8, respectfully.
Figure 10:
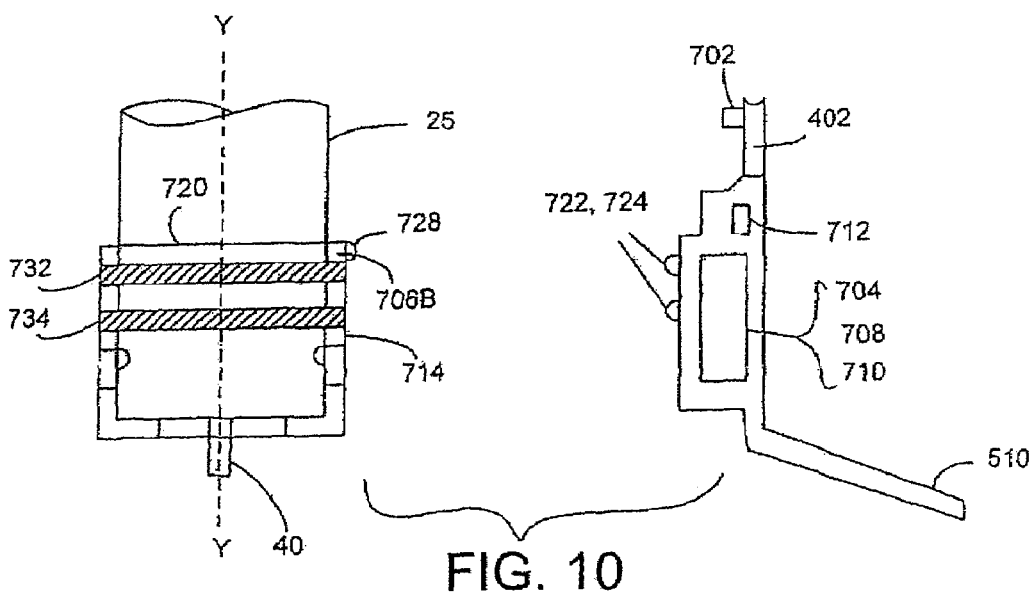

FIGS. 9-10 show detailed exemplary electrical contact configurations for the embodiments of FIGS. 7 and 8 respectively, differing in that the elements 704, 706A, 708, 710, 712, and 724 are on the "mouthpiece" side of the housing 402. The body 720 in those figures includes a molded protrusion 728 which is disposed to interferingly engage an operative portion of switch 702 extending from the inner surface of housing 402, as the canister 25 moves axially during a dose dispensing or actuation event. Such interfering engagement provides the signal to cause counter 704 to increment (or decrement). For simplicity, only two conductive strips 732, 734 are shown on body 720, and only a single connector 722 (for electrically coupling to a conductive strip on body 720, are shown in FIGS. 9 and 10. Any number of such connections can be implemented. With the relatively elongated body 720 of FIG. 10, there is ample space for many such connections.

While the above embodiments all disclose LED's for the displays (with associated drivers), other embodiments of the disclosure may include in addition, or alternatively, multi-digit displays (such as multidigit liquid crystal displays (LCDs) or LED's), which indicate signals representative of the number of doses dispensed (or remaining in) a canister. Moreover, yet other embodiments may indicate directly to a user, a visible signal (such as a flashing light) indicative of the occurrence of an actuation.

While the above described embodiments disclose user-viewable displays that are responsive to an event other than dispensing of a dose, such as opening of a cover, other embodiments may provide similar displays in response to detection of a dose dispensing event.

Figure 11:
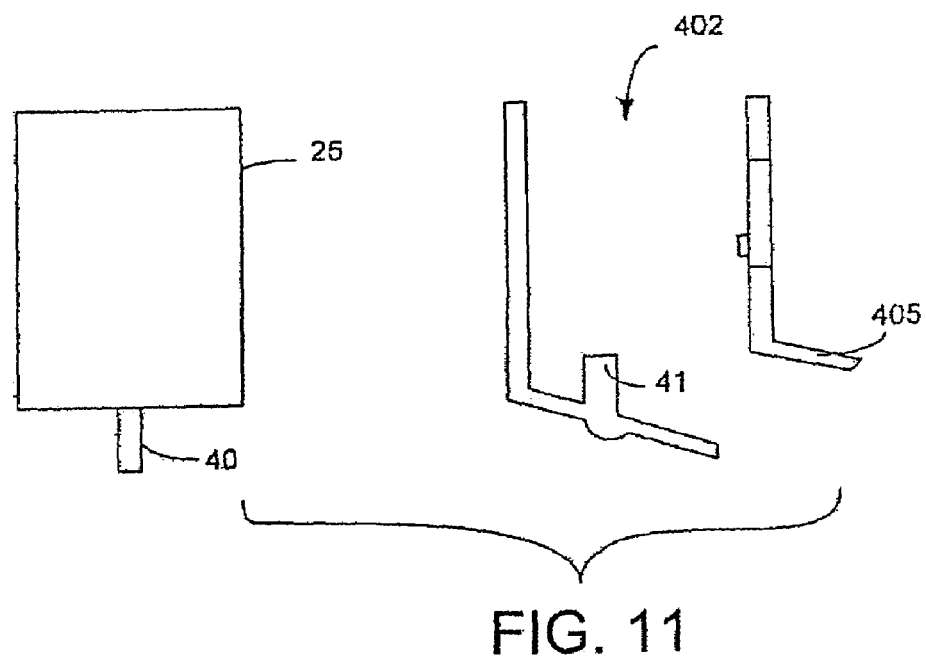
FIGS. 11-15 show alternative embodiments of canister state indicating assemblies constructed in accordance with the present disclosure.
Figure 12:
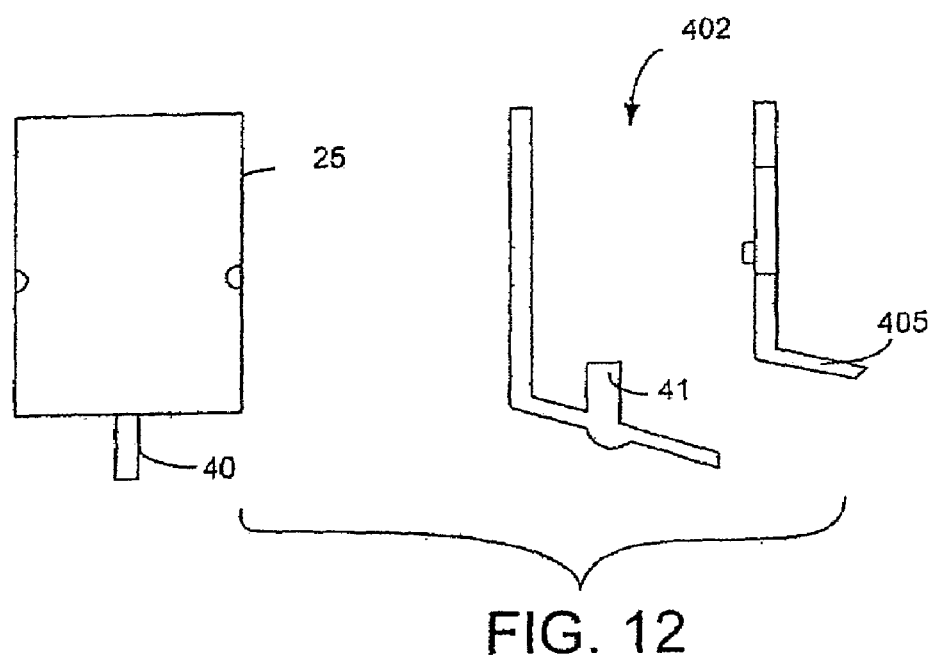
Figure 13:
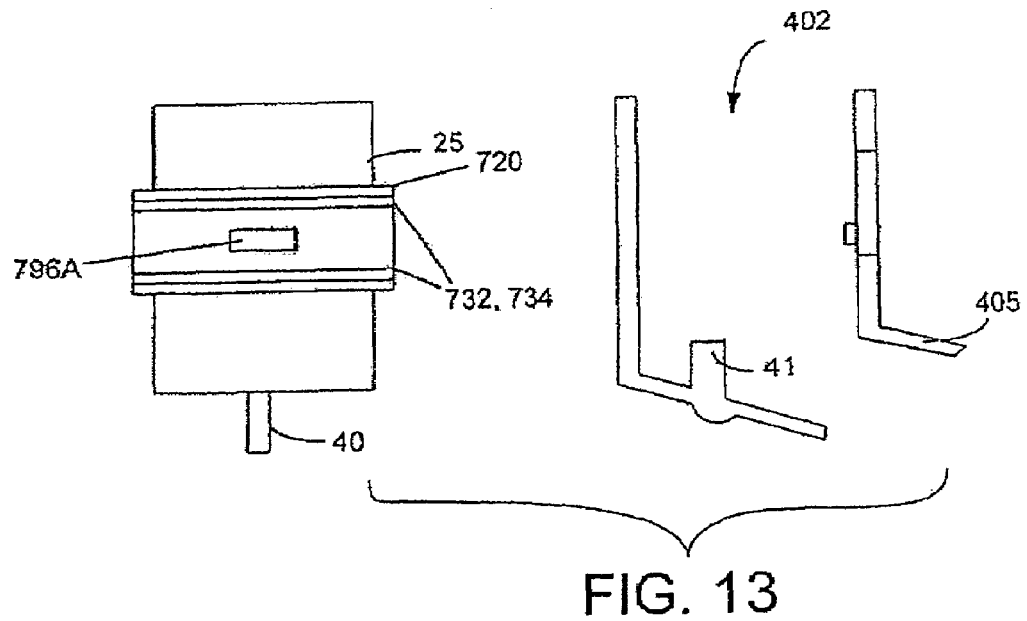

FIGS. 11-15 show alternative inhaler configurations embodying various forms of the disclosure. In FIGS. 11 and 12, the entire indicator assembly 700 is disposed on the housing 402. In FIG. 13, a memory 796A is canister-mounted, but is of a type that retains information after power is removed.

Figure 16:
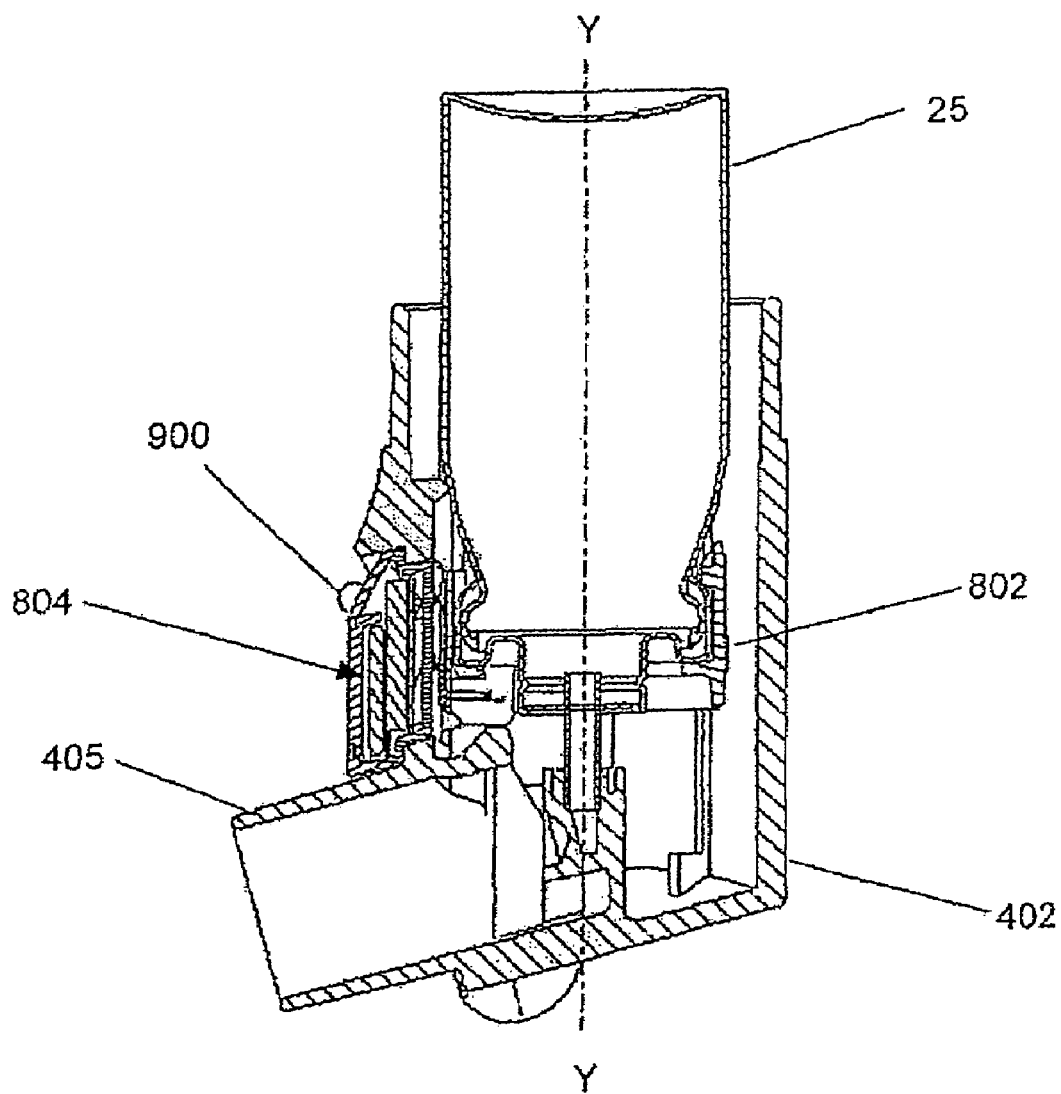
FIG. 16 shows a cross-sectional view of other exemplary embodiments of an inhaler and an canister state indicating assembly according to the present disclosure.
Figure 17:
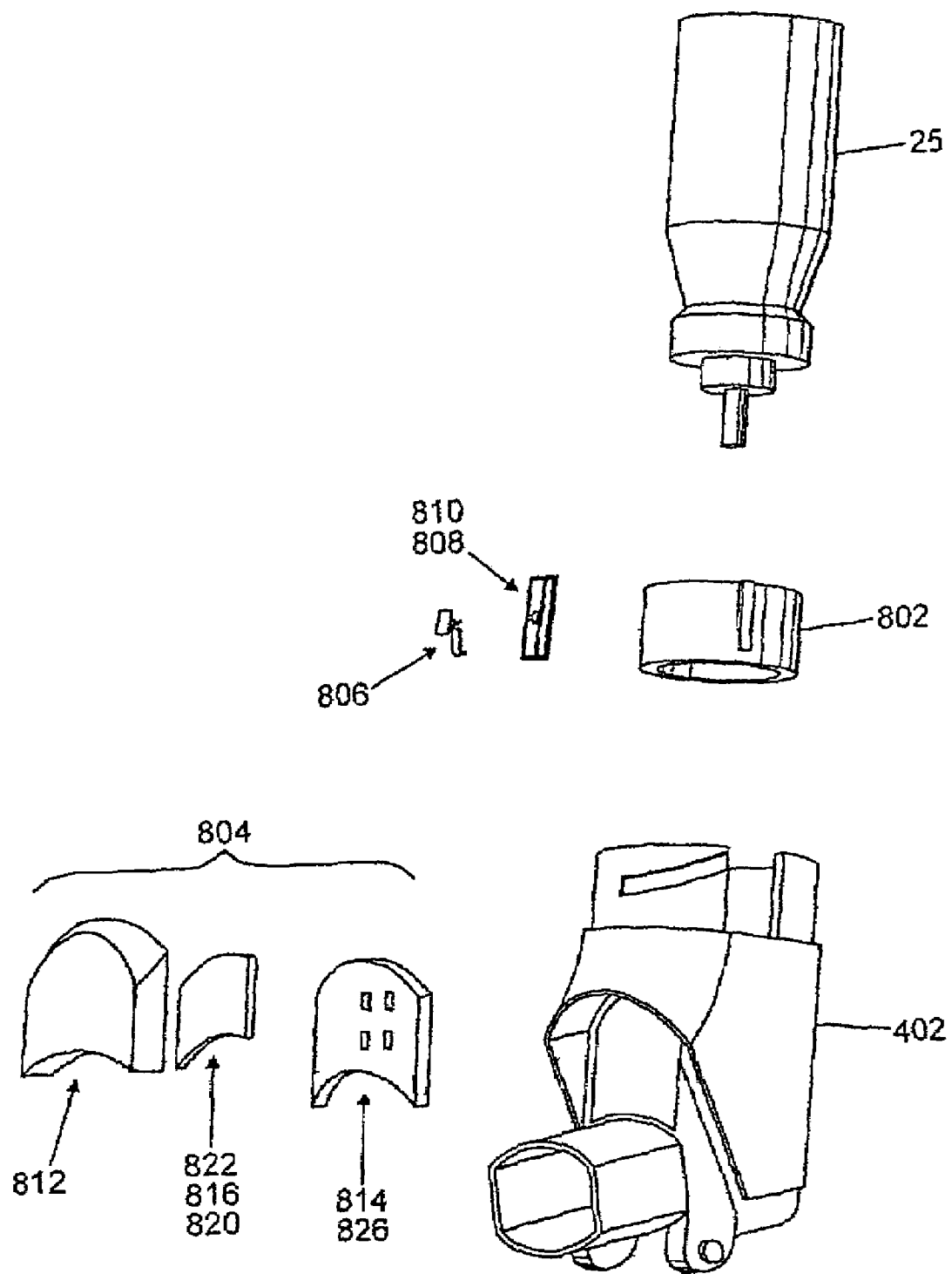
FIG. 17 shows an exploded perspective view of the inhaler and the canister state indicating assembly of FIG. 16.

In FIG. 16, the inhaler includes a can sleeve 802 attached to the canister 25, and an indicator unit 804, which includes the counter and the display, affixed to the housing 402. FIG. 17 shows an exploded view of the inhaler in FIG. 16. A switch 806, an identification (ID) chip 808 (for example a radio frequency identification (RFID) chip, or another form of readable device), and a component-bearing printed circuit board (PCB) 810 are attached to the can sleeve 802. In a exemplary form, the indicator unit 804 includes a front plastic housing 812, a rear plastic housing 814, a battery 816, a liquid crystal display (LCD) 820, a component-bearing printed circuit board (PCB) 822, and contacts 826. The contacts 826 are used to connect to the canister-mounted PCB 810 and ID chip 808 when the canister 25 is in the housing 402. The housing-mounted PCB 822 is configured with a microprocessor, which reads the information stored in the ID chip 808 through the contacts 826, and is responsive to that information, to recognize and accept the canister 25 to be used with the housing 402. The microprocessor also counts and saves the number of doses that have been taken in response to the "on" and "off" actuations of the switch 806. In this embodiment, there is no memory on the can sleeve 802 (or canister). Other embodiments may have memory on the sleeve (or canister).

The LCD display 820 indicates the recognition of the canister 25 by the housing 402 and the state of the canister 25 as a result of dose delivery actions. The front housing 812 and the rear housing 814 are preferably welded together by ultrasonic energy. The indicator unit 804 is preferably snap-fitted to the housing 402.

The ID chip 808 is configured with a unique machine-readable code to identify the canister 25. In the exemplary form of the disclosure, only when the indicator unit 804 on the housing recognizes the ID code of an associated canister, can the housing be used with that canister; otherwise, the counter will show "empty" or "error" information on the LCD, so that the user can know that he put the wrong canister in the housing. Only one canister matches with one housing. This ensures that the dose number saved in the memory in the microprocessor on the housing indicates the exact number of doses that have been taken from (or remain in) the canister. The ID chip also can be adapted for storage of additional information, e.g., indicative of the type of the drug in the canister, the expiry date, the number of doses, etc.

Figure 14:
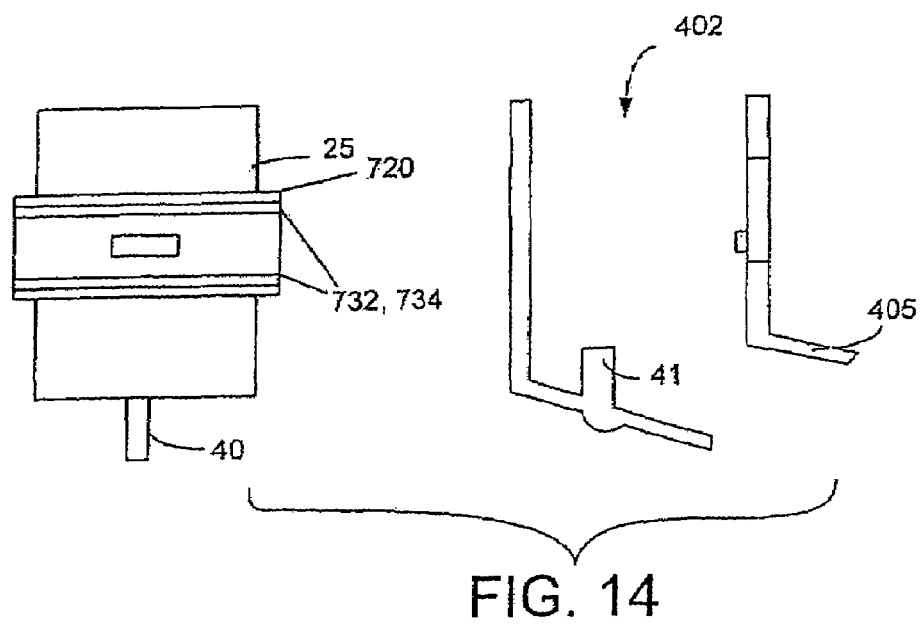
Figure 15:
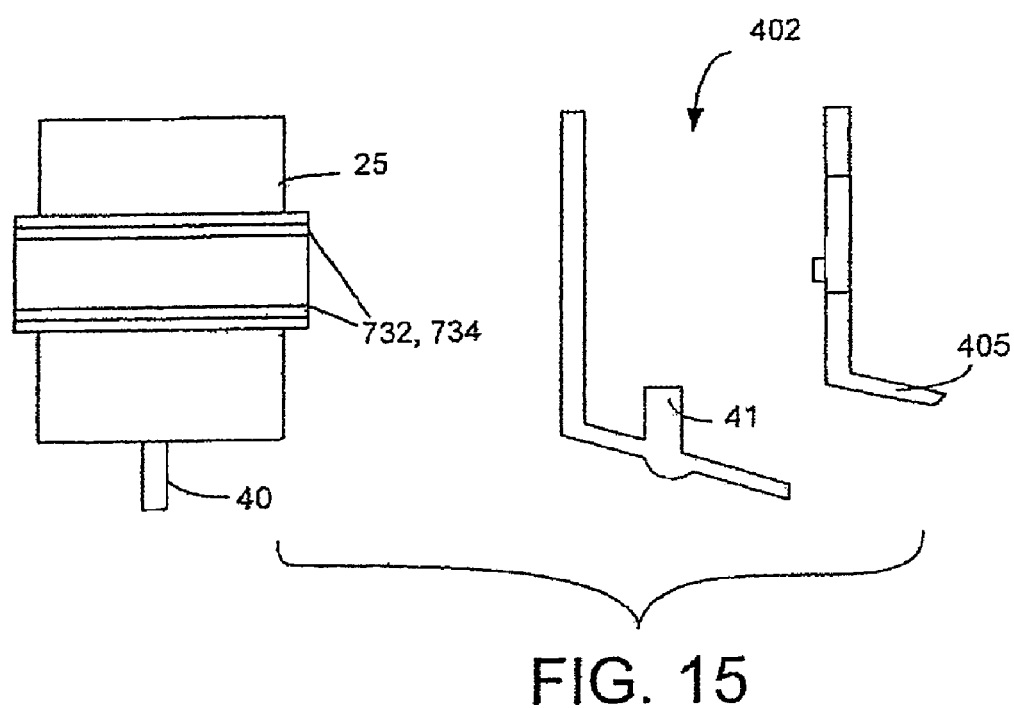
Figure 18:
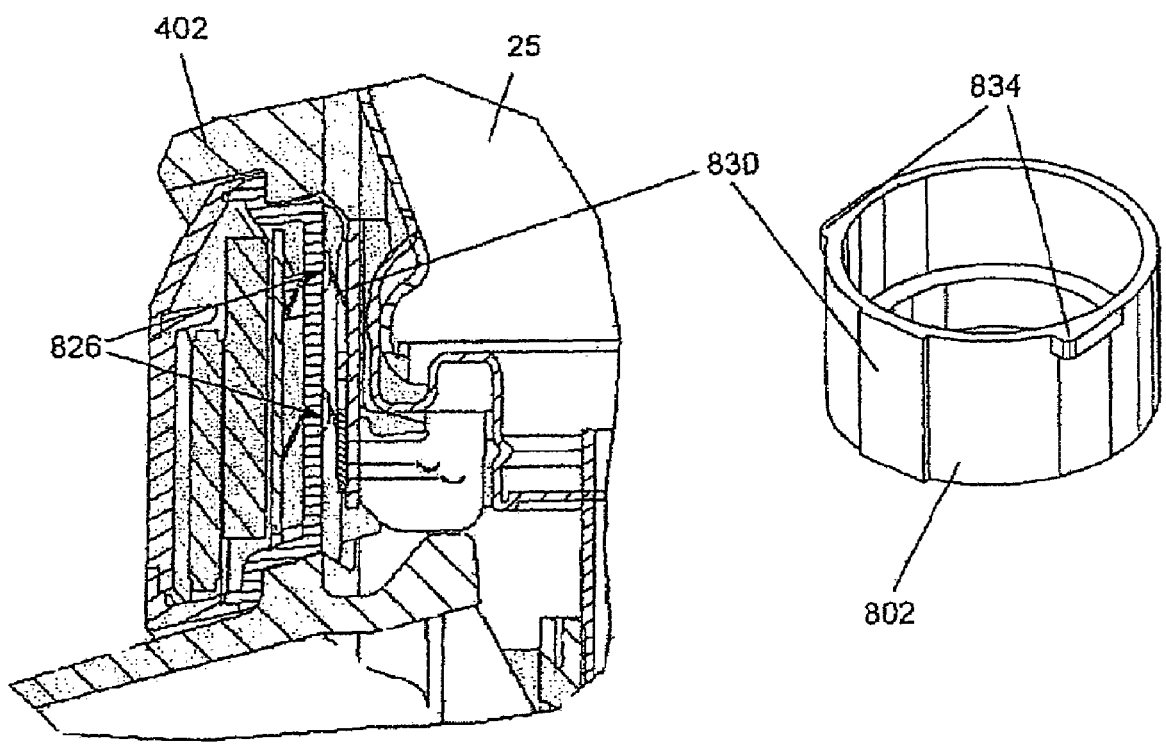
FIG. 18 shows a partial cross-sectional view of the inhaler of FIG. 16 shown with another exemplary embodiment of a sleeve member constructed in accordance with the present disclosure, and a perspective view of the sleeve.
Figure 19:
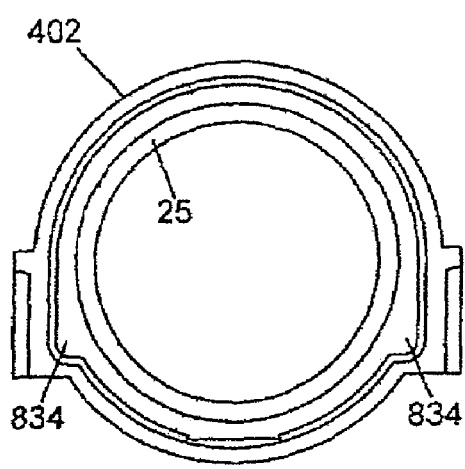
FIG. 19 illustrates an orientation mechanism according to one exemplary embodiment of the present disclosure.
Figure 20A:
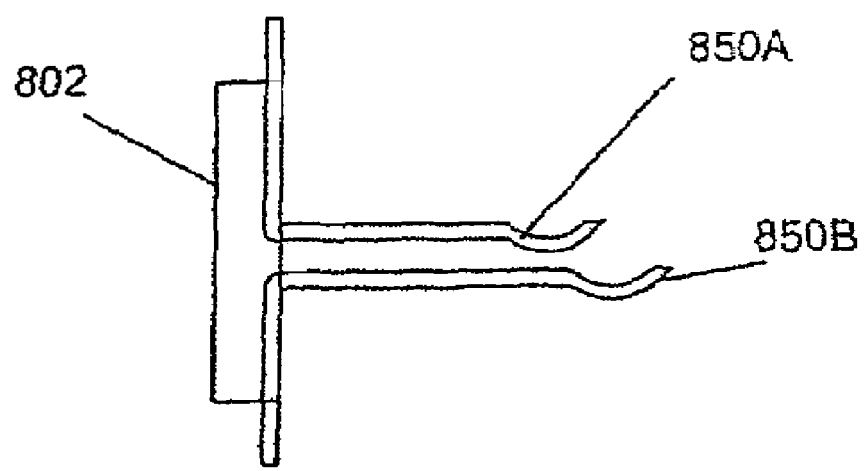
FIGS. 20A and 20B illustrate an exemplary embodiment of a switch assembly for use as part of a canister state indicating assembly of the present disclosure.
Figure 20B:
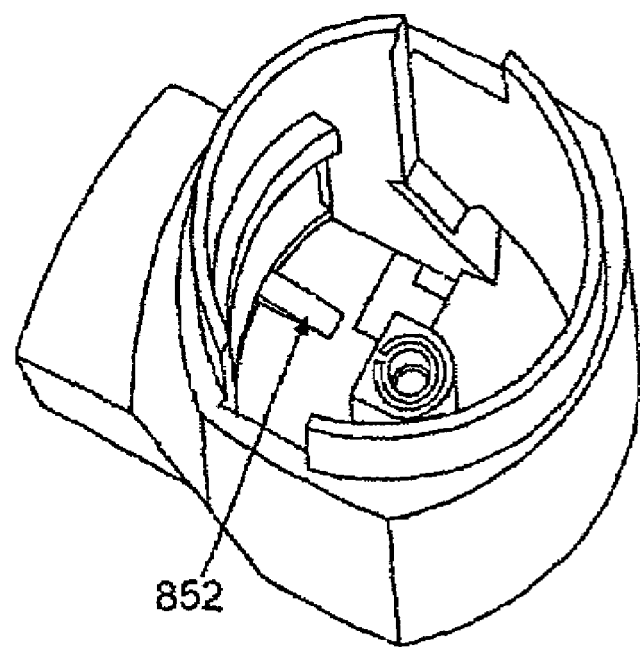

Both the sleeve 802 and the indicator unit 804 have contacts, so that the indicator unit 804 can read the ID of the canister 25 through contacts on the sleeve 802 and the indicator unit 804. The contacts 830 on the sleeve 802 and the contacts 826 on the indicator unit 804 are connected when the canister 25 is loaded in the housing 402, as shown in FIG. 18. Preferably, one set of the contacts 826 and contacts 830 attached to the housing or the sleeve, and the other set of the contacts 826 and contacts 830 are spring-loaded contacts. In the illustrated embodiment of FIG. 18, in order to ensure that every time the canister 25 is loaded into the housing 402, the contacts 830 and 826 are connected, the canister 25 is provided with alignment ribs 834 and the housing 402 defines alignment recesses to receive the ribs 834, as shown in FIG. 19. In an alternative form, the contacts 830 are provided with circular shapes on the outer surface of the sleeve 802, as shown in FIGS. 14 and 15, so that, even without an orientation mechanism, effected by the alignment ribs and recesses, the contacts 830 on the sleeve 802 can always be contact with the contacts 826 on the indicator unit 804.

FIGS. 20-23, show several switch mechanisms, which can be used with the present disclosure. One of skill in the art should understand that the switch design is not limited to the embodiments described herein, and that other switches in the art also can be used with the present disclosure. FIGS. 20A and 20B show one exemplary design of the switch assembly. The switch includes two contacts 850A and 850B attached to the bottom of the sleeve 802, as shown in FIG. 20A. The contacts 850A and 850B are spaced apart from each other. An electrically conductive bridge 852, as shown in FIG. 20B, is mounted to the housing at a position under the two contacts 850A and 850B. When the canister 25 with the sleeve 802 is pressed down, the two contacts 850A and 850B are electrically connected by the bridge 852. This closes the switch, which in turn causes the counter to count one more dose dispensed (or one less dose remaining).

When the canister 25 is released, the contacts 850A and 850B will be spaced apart from the bridge 852 and return to the open state.

Figure 21:
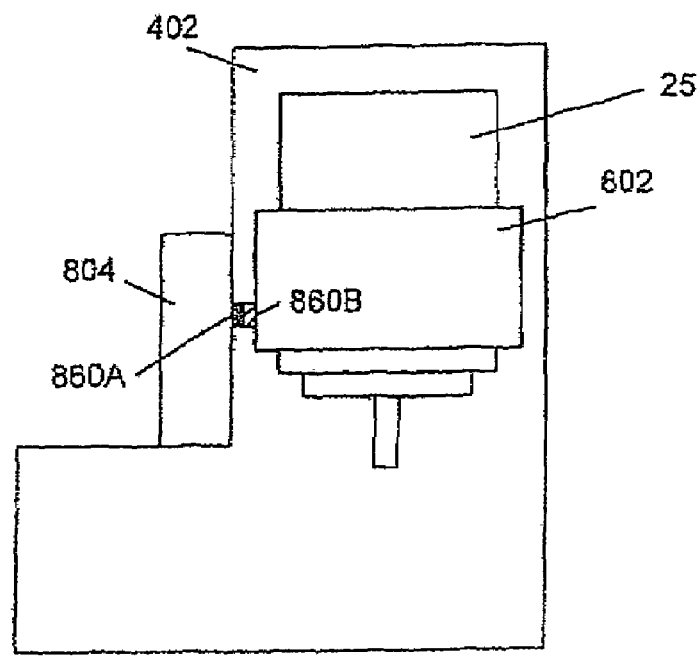
FIG. 21 illustrates another exemplary switch assembly according to the present disclosure.

FIG. 21 illustrates another exemplary switch, which includes contact 860A mounted on the indicator unit 804, and contact 860B mounted on the sleeve 802. In a released condition, the contacts 860A and 860B are not in the same level and are not in contact with each other (not shown in the figures). When the canister 25 is pressed down so as to administer a dose, the contact 860B on the sleeve 802 is in contact with the contact 860A on the indicator unit 804, as shown in FIG. 21, and the switch is closed, which causes the counter to increase (or decrease) one unit. When the canister 25 is released, the switch returns to the open state.

Figure 22:
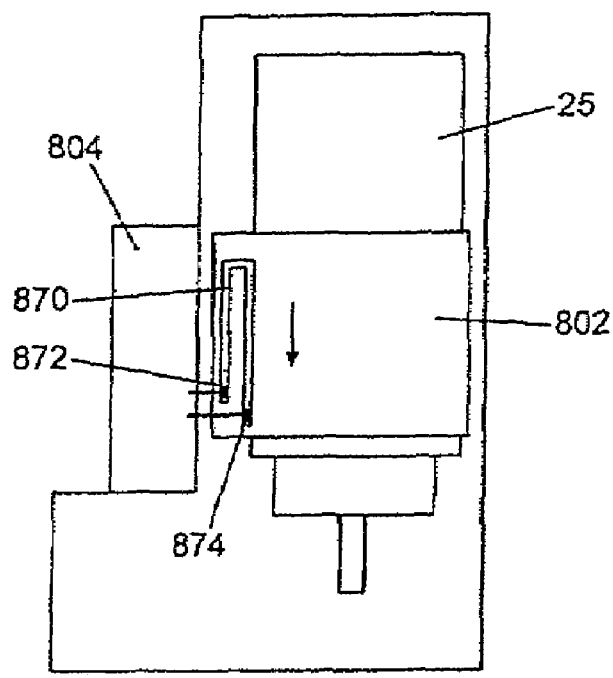
FIG. 22 illustrates a further exemplary switch assembly according to the present disclosure.

FIG. 22 illustrates a further exemplary switch, which is a relative movement switch. As shown in FIG. 22, the switch includes an electrically conductive track 870 mounted on the sleeve 802. The electrically conductive track 870 is characterized by a linear resistance. Two contacts 872 and 874, which are electrically coupled to the indicator unit 804, are placed on the track 870. As the canister 25 moves up and down, the length of the electrically conductive track 870 between the two contacts 872 and 874 varies, and in response to the change in length of the track between the two contacts 872 and 874, the resistance between the two contacts 872 and 874 will also change. The indicator unit 804 further includes a circuit to measure the change in resistance between the two contacts 872 and 874. If the change in resistance equates to a predetermined value, corresponding to the point of travel of the canister at which the canister dispenses medication, the counter in the indicator unit 804 will increment (or decrement) one unit, indicating that the patient has taken one dose.

Figure 23:
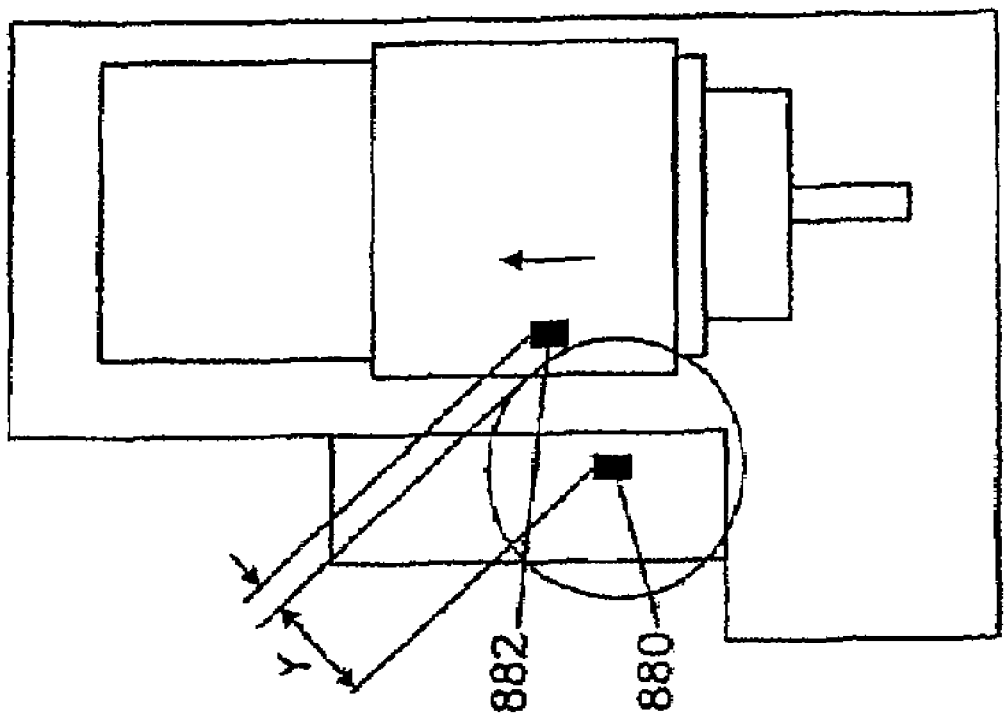
FIG. 23 illustrates yet another exemplary switch assembly according to the present disclosure.
Figure 23:
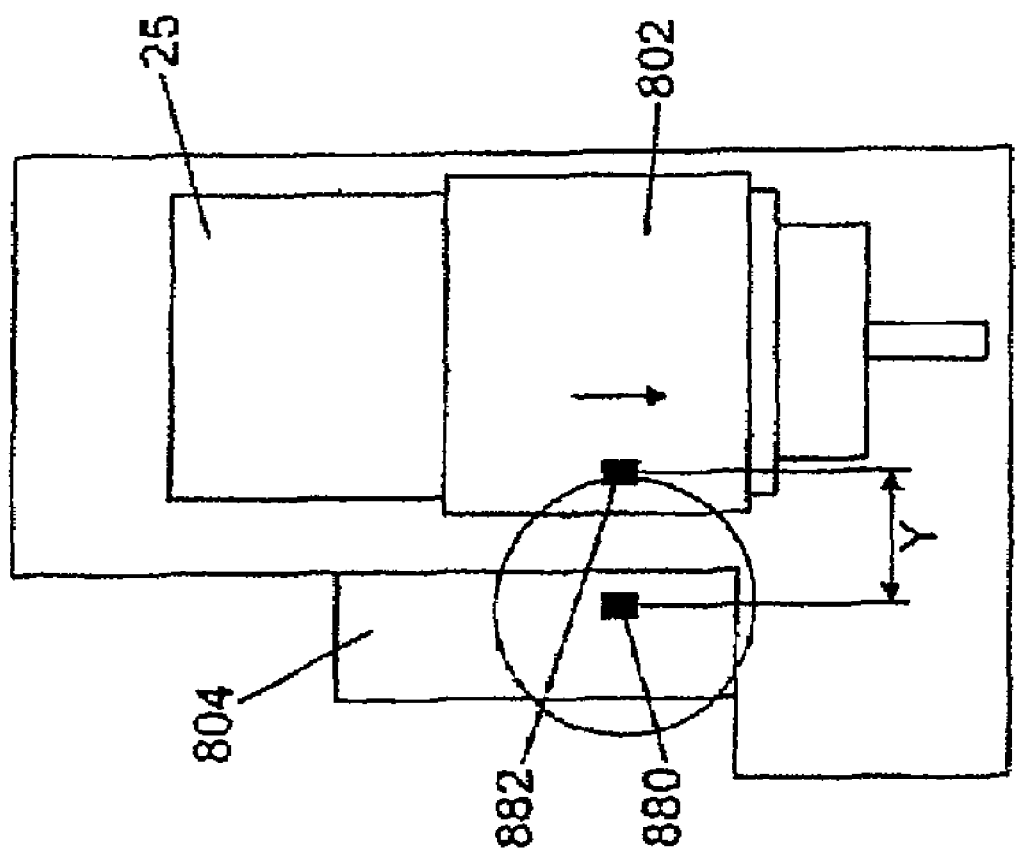

FIG. 23 shows a yet another exemplary switch, which is an inductive switch. The switch includes an inductive field generator 880, which is mounted on one of the indicator unit 804 and the can sleeve 802, and a detector 882, which is mounted on the other of the indicator unit 804 and the can sleeve 802 and is adapted to interfere with the field generated by the generator 880. The inductive field is characterized by a range, as schematically indicated by the circle in FIG. 23. As the canister 25 moves up and down, the detector 882 moves into and out of the range of the inductive field. The change of the state of the detector 882 (in or out of the field) will indicate a dose has been taken, and the indicator of the counter will increment (or decrement) one unit.

Figure 24A:
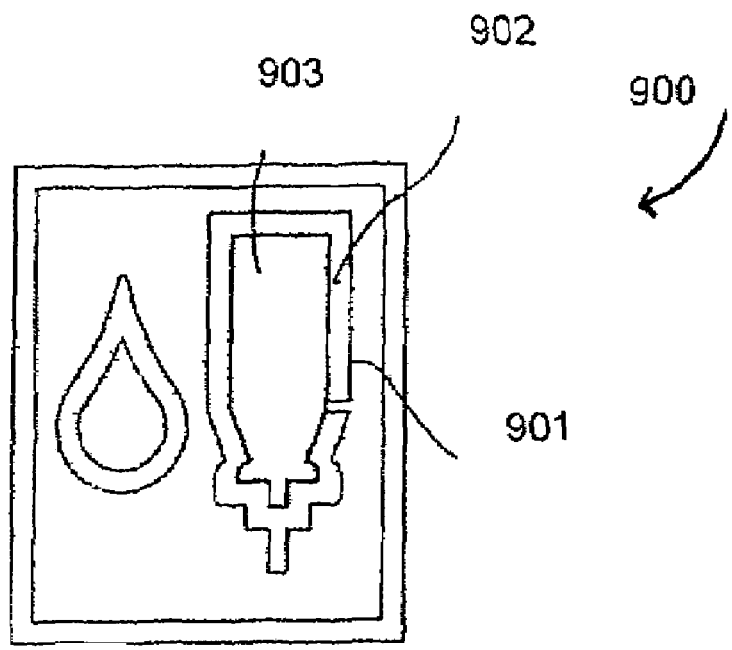
FIG. 24A illustrates an exemplary embodiment of a display of the present disclosure for use as part of a canister state indicating assembly.
Figure 24B:
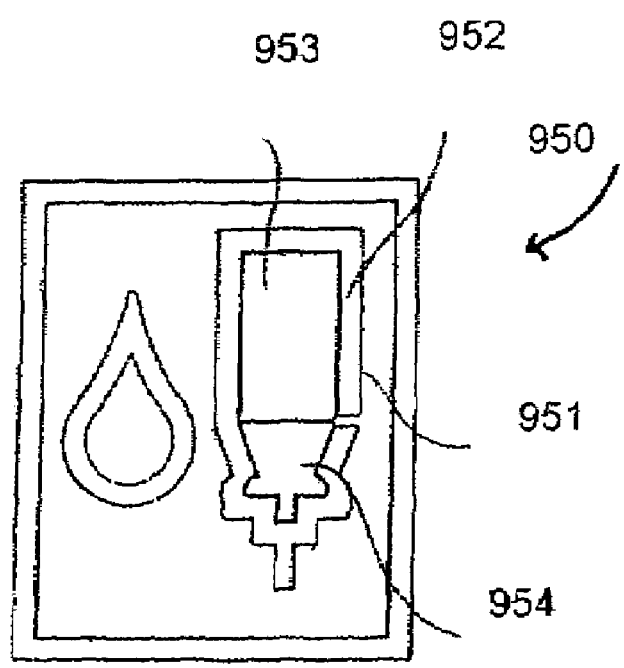
FIG. 24B illustrates another exemplary embodiment of a display of the present disclosure for use as part of a canister state indicating assembly.

In one exemplary form, a liquid crystal display (LCD) on the indictor unit shows the state of the canister, as shown in FIGS. 24A and 24B. LEDs could also be used to identify the state of the canister, such as the red-yellow-green configuration described above.

FIG. 24A shows a three-segment display system constituting a container state indicator 900 and including a graphic display device having an outline canister icon constituting an outer field 901 having an inner void region 902 and a medicament icon 903 constituting a medicament field disposed within the inner void region 902 of the outer field 901. The illustrated format provides, for example, an "all black" (or "filled") medicament icon (segment 2) and an outlined canister icon (segment 3) when segments 2 and 3 are "on", indicative a safe state where the canister contains more than X1 doses of medicament, where X1 is a predetermined number. The display provides an outlined canister icon (segment 3) when only segment 3 is on, (that is, when segment 3 is "on" and segment 2 is "off",) indicative a warning state where the canister contains less than X1 does of medicament.

FIG. 24B shows an alternative four-segment display system, constituting a container state 950 indicator including a graphic display device having an outline canister icon constituting an outer field 951 having an inner void region 952 and a first and second medicament icon 953 and 954 respectively, constituting first and second medicament fields disposed within the inner void region of the outer field. The illustrated format provides, for example, an "all black" (or "filled") medicament icon (segments 2 and 3) and an outlined canister icon (segment 4) when segments 2, 3 and 4 are "on", indicative a "safe" state where the canister contains more than X1 does of medicament, where X1 is a first predetermined number. The display provides a black outlined canister icon (segment 4) with black partial content (or "half-filled") medicament icon (segment 3) when segments 3 and 4 are "on", indicative a "caution" state where the canister contains fewer than X1 does of medicament, but more than X2 doses of medicament, where X2 is a second predetermined number, which is smaller than X1. The display provides an outlined canister icon (segment 4) with no content (or "empty") medicament icon when only segment 4 is "on", indicative a "warning" state where the canister contains fewer than X2 does of medicament.

In other embodiments different multi-segment displays may be used to indicate the canister state with more granularity.

The housing of the dispenser requires washing to avoid clogging of the stem block. To remind the patient to wash the dispenser, the LCD further includes a wash indicator, indicated as segment 1 in FIGS. 24A and 24B, which will turn on after a predetermined number of doses have been taken. Other forms of display icon configurations may be used to indicate the state of the canister and to remind the patient to wash the dispenser can be used.

In one embodiment, the dispenser further includes a mechanism (status button 900 in FIG. 16) to activate the LCD to show the canister state information for a relatively short time after each dose is taken. In that form, the dispenser further includes a status button, which controls the LCD. In another embodiment, the patient can check the status of the canister any time by pressing the status button to switch on the LCD. In a exemplary form of the disclosure, after a short time, the LCD automatically turns off to conserve battery energy.

The devices of the present disclosure are intended for use with any mammal that may experience the benefits of the disclosure. Foremost among such mammals are humans, although the disclosure is not intended to be so limited, and is applicable to veterinary uses. Thus, in accordance with the disclosure, "mammals" or "mammal in need" include humans as well as non-human mammals, particularly domesticated animals including, without limitation, cats, dogs, and horses.

The devices may be used for any drug formulation which may be advantageously administered to the lung or nasal passages in an mammal, to cure or alleviate any illness or its symptoms. A wide variety of medicaments, bioactive active substances and pharmaceutical compositions may be included in the dosage forms of the present disclosure. Examples of useful drugs include ace-inhibitors, acne drugs, alkaloids, amino acid preparations, anabolic preparations, analgesics, anesthetics, antacids, antianginal drugs, anti-anxiety agents, anti-arrhythmias, anti-asthmatics, antibiotics, anti-cholesterolemics, anti-coagulants, anti-convulsants, anti-depressants, anti-diabetic agents, anti-diarrhea preparations, antidotes, anti-emetics, anti-histamines, anti-hypertensive drugs, anti-inflammatory agents, anti-lipid agents, anti-manics, anti-nauseants, anti-nauseants, anti-neoplastics, anti-obesity drugs, anti-parkinsonism agents, anti-psychotics, anti-pyretics, anti-rheumatic agents, anti-spasmodics, anti-stroke agents, anti-thrombotic drugs, anti-thyriod preparations, anti-tumor drugs, anti-tussives, anti-ulcer agents, anti-uricemic drugs, anti-viral drugs, appetite stimulants or suppressants, biological response modifiers, blood modifiers, bone metabolism regulators, cardiovascular agents, central nervous system stimulates, cerebral dilators, cholinesterase inhibitors, contraceptives, coronary dilators, cough suppressants, decongestants, dietary supplements, diuretics, DNA and genetic modifying drugs, dopamine receptor agonists, endometriosis management agents, enzymes, erectile dysfunction therapies, erythropoietic drugs, expectorants, fertility agents, gastrointestinal agents, homeopathic remedies, hormones, hyper- and hypo-glycemic agents, hypercalcemia and hypocalcemia management agents, hypnotics, immunomodulators, immunosuppressives, ion exchange resins, laxatives, migraine preparations, motion sickness treatments, mucolytics, muscle relaxants, neuromuscular drugs, obesity management agents, osteoporosis preparations, oxytocics, parasympatholytics, parasympathomimetics, peripheral vasodilators, prostaglandins, psychotherapeutic agents, psycho-tropics, stimulants, respiratory agents, sedatives, smoking cessation aids, sympatholytics, systemic and non-systemic anti-infective agents, terine relaxants, thyroid and anti-thyroid preparations, tranquilizers, tremor preparations, urinary tract agents, vasoconstrictors, vasodilators, and combinations thereof.

The disclosure may be embodied in other specific forms without departing from the spirit or essential characteristics thereof. The present embodiments are therefore to be considered in all respects illustrative and not restrictive, the scope of the disclosure being indicated by the appended claims rather than by the foregoing description, and all changes which come within the meaning and range of equivalency of the claims are therefore intended to be embraced therein.

What is claimed is:

1. A medicament inhaler assembly, comprising:
   a housing defining a central void region disposed along a central axis;
   a medicament container having an internal medicament containing reservoir, and extending along a container axis, and having at one end thereof, a dispensing port extending along said central axis, said dispensing port being coupled to said medicament containing reservoir, said medicament container containing a medicament disposed in said medicament containing reservoir, said medicament being in the form of a plurality of doses;
   a dispensing means for dispensing said medicament from said medicament container, wherein in response to a user-induced motion said medicament container translates relative to said housing in a first direction along said central axis causing said medicament to be dispensed from said dispensing port;
   an identification means for identifying said medicament container, said identification means configured for presenting information indicative of an identity of said container, wherein if said identity of said container is associated with said housing a first identifier is sent, and if said identity of said container is not associated with said housing a second identifier is sent;
   a sleeve attached to said medicament container, wherein said identification means is attached to said sleeve;
   a detector attached to said housing and adapted to detect said presented information from said identification means when said container is disposed in said central void region of said housing, wherein when said identification means sends said first identifier said detector generates a valid signal in response and when said identification means sends said second identifier said detector sends an invalid signal; and
   a container state indicator assembly attached to said housing and said container, said container state indicator assembly including a detection means adapted for detecting a medicament dispensing motion of said medicament container relative to said housing, said container state indicator assembly further including a signaling means adapted for generating a signal indicative of a state of said medicament container.

2. The assembly according to claim 1, wherein said states of said medicament container include a first state and a second state.

3. The assembly according to claim 2, wherein said first state is indicative of said medicament containing reservoir containing at least a first predetermined number of doses, and said second state is indicative of said medicament containing reservoir containing less than said first predetermined number of doses.

4. The assembly according to claim 3, wherein said container state indicator assembly includes a graphic display device having an outer field with an inner void region and a medicament field disposed within said inner void region, wherein when said medicament containing reservoir includes at least said first predetermined number of doses said outer field and said medicament field are both turned on, and when said medicament containing reservoir includes less than said first predetermined number of doses only said outer field is turned on.

5. The assembly according to claim 4, wherein said outer field is container-shaped.

6. The assembly according to claim 4, wherein said outer field has a rectangular shape.

7. The assembly according to claim 4, wherein said outer field has a triangular shape.

8. The assembly according to claim 1, wherein said medicament container has one of at least three states.

9. The assembly according to claim 8, wherein said three states include a first state, a second state and a third state, wherein said first state is indicative of said medicament containing reservoir containing at least a first predetermined number of doses, said second state is indicative of said medicament containing reservoir containing fewer than said first predetermined number of doses but more than a second predetermined number of doses, said second state being a caution state, and said third state is indicative of said medicament containing reservoir containing fewer than said second predetermined number of doses.

10. The assembly according to claim 9, wherein said container state indicator assembly includes a graphic display device having an outer field defining an inner void region, and first and second medicament fields disposed within said inner void region of said outer field, wherein when said medicament containing reservoir includes at least said first predetermined number of doses said outer field and said first and second medicament fields are all turned on, when said medicament containing reservoir includes less than said first predetermined number of doses and more than said second predetermined number of doses said outer field and said first medicament field only are turned on, and when said medicament containing reservoir includes less than said second predetermined number of doses only said outer field is turned on.

11. The assembly according to claim 10, wherein said outer field is container-shaped.

12. The assembly according to claim 10, wherein said outer field has a rectangular shape.

13. The assembly according to claim 10, wherein said outer field has a triangular shape.

14. The assembly according to claim 1, wherein said container is an aerosol container.

15. The assembly according to claim 14, wherein said medicament is selected from a group consisting of ace-inhibitors, acne drugs, alkaloids, amino acid preparations, anabolic preparations, analgesics, anesthetics, antacids, anti-anginal drugs, anti-anxiety agents, anti arrhythmias, anti-asthmatics, antibiotics, anti-cholesterolemics, anti-coagulants, anti-convulsants, anti-depressants, anti-diabetic agents, anti-diarrhea preparations, antidotes, anti-emetics, anti-histamines, anti-hypertensive drugs, anti-inflammatory agents, anti-lipid agents, anti-manics, anti-nauseants, anti-nauseants, anti-neoplastics, anti-obesity drugs, anti-parkinsonism agents, anti-psychotics, anti-pyretics, anti-rheumatic agents, anti-spasmodics, anti-stroke agents, anti-thrombotic drugs, anti-thyriod preparations, anti-tumor drugs, anti-tussives, anti-ulcer agents, anti-uricemic drugs, anti-viral drugs, appetite stimulants or suppressants, biological response modifiers, blood modifiers, bone metabolism regulators, cardiovascular agents, central nervous system stimulates, cerebral dilators, cholinesterase inhibitors, contraceptives, coronary dilators, cough suppressants, decongestants, dietary supplements, diuretics, DNA and genetic modifying drugs, dopamine receptor agonists, endometriosis management agents, enzymes, erectile dysfunction therapies, erythropoietic drugs, expectorants, fertility agents, gastrointestinal agents, homeopathic remedies, hormones, hyper- and hypo-glycemic agents, hypercalcemia and hypocalcemia management agents, hypnotics, immunomodulators, immunosuppressives, ion exchange resins, laxatives, migraine preparations, motion sickness treatments, mucolytics, muscle relaxants, neuromuscular drugs, obesity management agents, osteoporosis preparations, oxytocics, parasympatholytics, parasympathomimetics, peripheral vasodilators, prostaglandins, psychotherapeutic agents, psycho-tropics, stimulants, respiratory agents, sedatives, smoking cessation aids, sympatholytics, systemic and non-systemic anti-infective agents, terine relaxants, thyroid and anti-thyroid preparations, tranquilizers, tremor preparations, urinary tract agents, vasoconstrictors, vasodilators, and combinations thereof.

16. The assembly according to claim 1, wherein said identification means includes an RFID device.

17. The assembly according to claim 1, wherein said detector is coupled to said identification means by a spring-loaded contact assembly, said spring-loaded contact assembly including fixed contacts attached to one of said housing and said medicament container, and including spring-loaded contacts attached to the other of said housing and said medicament container.

18. The assembly according to claim 1, wherein said container state indicator assembly is coupled to said medicament container by a spring-loaded contact assembly, said spring-loaded contact assembly including fixed contacts attached to one of said housing and said medicament container, and including spring-loaded contacts attached to the other of said housing and said medicament container.

19. The assembly according to claim 1, wherein said detector includes a display for indicating said valid or invalid signal generated by said detector.

20. The assembly according to claim 1, wherein said container state indicator assembly includes a display for indicating said signal generated by said container state indicator assembly.

21. The assembly according to claim 20, wherein said display is a liquid crystal display (LCD).

22. The assembly according to claim 20, wherein said display includes a light emitting diode (LED) device.

23. The assembly according to claim 20, wherein said display includes a switch, which turns on said display in response to said user-induced motion of said medicament container relative to said housing and then turns off said display after a relatively short period of time.

24. The assembly according to claim 20, wherein said display includes a switch with a control button accessible from an external surface of the assembly, wherein said switch turns on said display when a user depresses said control button and then turns off said display after a relatively short period of time.

25. The assembly according to claim 20, wherein said display includes a graphic display and a numeric display.

26. The assembly according to claim 1, wherein said sleeve is located proximate said dispensing port.

27. The assembly according to claim 1, wherein said sleeve is located at or near an intermediate portion of said container.

28. The assembly according to claim 1, wherein said sleeve includes at least one longitudinal rib and said housing defines at least one groove for receiving said at least one longitudinal rib to maintain a desired alignment of said medicament container in said housing.

29. The assembly according to claim 1, wherein said container state indicator assembly includes a memory device for saving the state of said medicament container.

30. The assembly according to claim 1, wherein said container state indicator assembly includes a switch assembly operatively connected to said medicament container and said housing, and a counter for counting the number of doses dispensed from said medicament container, wherein said medicament dispensing motion activates said switch assembly, which in turn activates said counter to count one unit.

31. The assembly according to claim 30, wherein said switch assembly includes a substantially U-shaped electrically conductive track attached to one of said medicament container and said housing, and two contacts attached to the other of said medicament container and said housing and electrically connected to said track, wherein a dispensing movement of said medicament container relative to said housing causes the length of said track between said two contacts to change, that in turn activates said counter to count one unit.

32. The assembly according to claim 30, wherein said switch assembly includes an inductive field generator attached to one of said medicament container and said housing, and an inductive detector attached to the other of said medicament container and said housing, wherein said inductive detector senses a movement of said inductive field generator relative to said inductive detector, and in turn activates said counter to count one unit.

* * * * *